(12) United States Patent
Baldwin et al.

(10) Patent No.: US 11,648,211 B2
(45) Date of Patent: May 16, 2023

(54) NANOENCAPSULATED COMBINATION DRUG FORMULATIONS

(71) Applicant: Northeastern University, Boston, MA (US)

(72) Inventors: Paige Baldwin, Cambridge, MA (US); Srinivas Sridhar, Newton, MA (US); Bijay Singh, Cambridge, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 17/030,286

(22) Filed: Sep. 23, 2020

(65) Prior Publication Data
US 2021/0085619 A1    Mar. 25, 2021

Related U.S. Application Data

(60) Provisional application No. 62/903,974, filed on Sep. 23, 2019.

(51) Int. Cl.
| | |
|---|---|
| *A61K 9/51* | (2006.01) |
| *A61K 9/10* | (2006.01) |
| *A61K 45/06* | (2006.01) |
| *B82Y 5/00* | (2011.01) |

(52) U.S. Cl.
CPC ............. *A61K 9/5184* (2013.01); *A61K 9/10* (2013.01); *A61K 45/06* (2013.01); *B82Y 5/00* (2013.01)

(58) Field of Classification Search
CPC ........ A61K 9/5184; A61K 9/10; A61K 45/06; B82Y 5/00
See application file for complete search history.

(56) References Cited

U.S. PATENT DOCUMENTS

2016/0206615 A1 *  7/2016  Tangutoori ........... A61K 9/1272

OTHER PUBLICATIONS

A Beletsi, et al, Biodistribution Properties of Nanoparticles Based on Mixtures of PLGA with PLGA-PEG Diblock Copolymers, 298 Intl. J Pharmaceu. 233 (Year: 2005).*
Fabienne Danhier, et al, Active and Passive Tumor Targeting of a Novel Poorly Soluble Cyclin Dependent Kinase Inhibitor, JNJ-7706621,392 Intl. J Pharmaceut. 20 (Year: 2010).*
Che-Ming Hu, Liangfang Zhang, Nanoparticle-Based Combination Therapy Toward Overcoming Drug Resistance in Cancer, 83 Biochem. Pharmacol. 1104 (Year: 2012).*
David Alagpulinsa, etal, Dinaciclib, a CDK Inhibitor, Impairs Homologous Recombination and Sensitizes Multiple Myeloma Cells to PARP Inhibition, 124 BLOOD 479 (Year: 2014).*
Yuqiao Shen, et al, Trapping Poly(ADP-Ribose) Polymerase, 353 J Pharmacol. Exp. Ther. 446 (Year: 2015).*
Shawn F. Johnson, et al., The CDK Inhibitor Dinaciclib Sensitizes Triple-Negative Breast Cancer Cells to PARP Inhibition, 73 Cancer Res. 1788 (Year: 2013).*
Gary K. Scott, et al, ERpS294 is a Biomarker of Ligand or Mutational Era Activation and a Breast Cancer Target for CDK2 Inhibition , 8 ONCOTARGET 83432 (Year: 2017).*
Jason P.W. Carey, et al, Synthetic Lethality of PARP Inhibitors in Combination with MYC Blockade is Independent of BRCA Status in Triple-Negative Breast Cancer, 78 Cancer Res. 742 (Year: 2018).*
Lewis et al., "Nanotherapeutics for inhibition of atherogenesis and modulation of inflammation in atherosclerotic plaques" Cardiovasc. Res. 109, pp. 283-293 (2016).
Rajan et al., "A phase I combination study of olaparib with cisplatin and gemcitabine in adults with solid tumors" Clin. Cancer Res. 18, pp. 2344-2351 (2012).
De Jong et al., "Drug delivery and nanoparticles:applications and hazards" Int. J. Nanomedicine 3, pp. 133-149 (2008).
Davis et al., "Nanoparticle therapeutics: an emerging treatment modality for cancer" Nat. Rev. Drug Discov. vol. 7, pp. 771-782 (2008).
Zhang et al., "A nano-liposome formulation of the PARP inhibitor Talazoparib enhances treatment efficacy and modulates immune cell populations in mammary tumors of BRCA-deficient mice" Theranostics. 2019, vol. 9, Issue 21, pp. 6224-6238.
Baldwin et al., "Nanoformulation of Talazoparib Delays Tumor Progression and Ascites Formation in a Late Stage Cancer Model", Front Oncol. 2019; vol. 9, 12 pages.
Danhier et al., "Active and passive tumor targeting of a novel poorly soluble cyclin dependent kinase inhibitor, JNJ-7706621", International Journal of Pharmaceuticals, 392 (2010) pp. 20-28.
Alagpulinsa et al., "Dinaciclib, a CDK Inhibitor, Impairs Homologous Recombination and Sensitizes Multiple Myeloma Cells to PARP Inhibition". Blood (2014) 124(21), 3 pages.
Shen et al., "Trapping Poly(ADP-Ribose) Polymerase", J. Pharmacol Exp Ther 353:pp. 0446-0457, Jun. 2015.
Hu et al.,"Nanoparticle-based combination therapy toward overcoming drug resistance in cancer", hemical Pharmacology 83 (2012) pp. 1104-1111.
Beletsi et al., "Biodistribution properties of nanoparticles based on mixtures of PLGA with PLGA-PEG diblock copolymers". International Journal of Pharmaceutics 298 (2005) pp. 233-241.

(Continued)

*Primary Examiner* — Sean M Basquill
(74) *Attorney, Agent, or Firm* — Verrill Dana, LLP

(57) ABSTRACT

Pharmaceutical formulations (nanococktails) include two or more nanoparticulate delivery vehicles each including an active agent. The nanococktails can be formulated at any ratio of active agents by changing the ratio of nanoparticulate delivery vehicles in the nanococktail. The nanoparticulate delivery vehicles can have matched surface potential to prevent aggregation. The nanoparticulate delivery vehicles of the combined formulation are designed to provide each active agent with desired, preferably overlapping therapeutic windows and a specifically selected pharmacokinetic and pharmacodynamic profile when the nanococktail is administered to a subject. Each of the nanoparticulate delivery vehicles can be designed to enhance solubility, duration of action, targeting, stability, and to program release while preventing degradation of an active agent and preventing side effects, toxicity, and tolerability issues in a subject.

9 Claims, 20 Drawing Sheets

(56) References Cited

OTHER PUBLICATIONS

Hong et al., "Five servere COVID-19 pneumonia patients treated with triple combination therapy with lopinavir/ritonavir, hydroxychloroquine, and interferon β-1b", International Journal of Antimicrobial Agents 56 (2020) 106052, pp. 1-3.

Dhawan et al., "Efficacy of hematologic toxicity of caboplatin and talazoparib combination therapy in BRCA mutated patients.", ascopubs.org/doi/abs/10.1200/JCO.2016.34.15_suppl.2557 Abstract Only.

Chou et al., "CompuSyn for Drug Combinations and for General Dose-Effect Analysis", 2005, combosyn.com/feature.html.

* cited by examiner

FIG. 11A

NANOENCAPSULATED COMBINATION DRUG FORMULATIONS

CROSS-REFERENCE TO RELATED APPLICATIONS

This application claims priority to U.S. Provisional Application No. 62/903,974, filed 23 Sep. 2019, the entirety of which is incorporated herein by reference.

BACKGROUND

Combination therapy involves administration of more than one therapeutic agent to a patient. Combination therapy can be utilized for the treatment of a number of diseases or conditions including infections, cancers, and cardiovascular disease [1-5]. While combination therapy is often used in an effort to enhance patient response, such as to avoid development of resistance to a drug or to treat resistance, combination therapy is plagued by tolerability issues and side effects [3,6,7]. The lack of tolerability may result in a dose reduction or a delay of treatment, and may render the combination therapy less effective than a single agent.

During the HIV/AIDS pandemic, the concept of a drug cocktail, a combination of protease inhibitors taken with reverse transcriptase inhibitors, brought tolerability to the forefront with AZT combination therapies. Today, many therapeutic combinations and drug cocktails remain at the forefront of care. While drug cocktails have advanced, tolerability and side effects also remain as key issues. The issue of tolerability is particularly prevalent in the treatment of cancers, in which drug cocktails have become the standard of care, but often combinations that appear promising are limited by adverse events in the clinic.

The issue of tolerability often arises due to the formulation administered to the patient and not due to the active agents in the formulation. The formulation can provide the active agents to the patient, but thereafter the effects of the active agents are not in control of the health professional. It is particularly frustrating that in many cases the combination therapy is proven, but patient delivery by formulation of the combination therapy is plagued by different pharmacokinetics, durations of action, or different serum half-lives of the active agents. The active agents may accumulate in different areas of a patient, further frustrating attempts to combine therapies.

Nanoparticles, particles about 1-1000 nm in size, have been studied for the delivery of therapeutics due to their potential delivery benefits, including the ability to reduce toxicity while maintaining therapeutic efficacy [8,9]. However, the development of nanoparticles for delivery of therapeutic agents has not solved many of the current delivery and toxicity issues associated with combination therapies.

SUMMARY

The present technology provides formulations containing combinations of nanoparticulate delivery vehicles which can be individually tailored for appropriate administration of combinations of active agents. The nanoparticulate delivery vehicles can be mixed into a pharmaceutical formulation in any ratio to meet the needs determined by patient conditions (e.g., for an immunocompromised patient). The design of the nanoparticulate delivery vehicles can include adjusting the duration of action of an active agent. The nanoparticulate delivery vehicles can be combined in a pharmaceutical formulation to provide and optimize overlapping therapeutic windows of the active agents for delivery of a highly effective combination therapy (a nanococktail) to a patient. The formulation is configured for coordinated deliver of two or more active agents. Coordinated delivery can result in an increase in the overlap of therapeutic windows of the active agents. It also may include an increase in duration of action for one or more of the agents, as well as a decrease in toxicity, an increase in solubility, an improvement in pharmacokinetics, a decrease in adverse effects (e.g., accumulation in an undesired location, such as the liver), or a combination thereof. The technology can provide methods of treating a patient that will minimize tolerability or side effects while maximizing delivery of one or more active agents to a targeted area or to the circulatory system of a patient (an increase in effectiveness of combined therapy). The technology can be used to combine diagnostic or imaging agents together with therapeutic agents. The technology can provide methods of making nanoparticulate pharmaceutical formulations that give the caregiver options to titrate and to tailor the formulation just before administration to a specific patient, taking into account, for example, the patient's lab results. The technology enables a caregiver to take into consideration a matrix of variables (e.g., patient conditions, degradation, serum half-life, targeting, toxicity) before administering two or more active agents to a patient, thereby giving the caregiver pre-planned control over the active agents.

The present technology provides a pharmaceutical formulation that includes a first nanoparticulate delivery vehicle containing at least a first active agent and a second nanoparticulate delivery vehicle containing a second active agent. The first and second delivery vehicles can be, for example, polymeric nanoparticles, metallic nanoparticles, liposomes, micelles, or solid lipid nanoparticles. The delivery vehicles provide control over the targeting, release, and duration time of the active agent associated with the delivery vehicle when administered to a subject. The active agent can be incorporated within the delivery vehicle, such as embedded within a polymeric nanoparticle, either within or encapsulated by the polymer chains, or it can be covalently or non-covalently attached to the surface of the nanoparticle. For liposomes, the active agent can be solubilized within the lumen of the liposomes, or embedded within the lipid bilayer, or attached to the outer surface of the lipid bilayer. The subject can be a human or other mammal. The delivery vehicles are configured for coordinated delivery of the first and second active agents when the formulation is administered to a subject in need thereof. Coordinated delivery provides one or more pharmacokinetic and/or pharmacodynamic properties that are improved compared to deliver of individual active agents whose pharmacokinetics and/or pharmacodynamics have not been optimized for coordination with another active agent. Coordinated delivery can provide, for example, a greater therapeutic index, longer duration of action, longer serum half-life, higher solubility, greater therapeutic efficacy, reduced toxicity, reduced side effects, or reduced degradation of one or all of the active agents in the combined formulation. The two or more nanoparticulate delivery vehicles can contain the same or different active agents. If they contain the same active agent, the different vehicles will differ in some aspect of administration of the active agent, such as time of release or target.

In the pharmaceutical formulations described above, two or more nanoparticulate delivery vehicles are combined in the same formulation, forming a single physical composition. Alternatively, the two or more nanoparticulate delivery vehicles can be provided as separate compositions, optionally as separate formulations, which can be provided in separate containers and provided as a pharmaceutical kit. The kit can have additional packaging, instructions for use, and optionally certain reagents or devices required or useful for use of the kit, such as for mixing, measuring, quantifying, detecting, or administering the vehicles. The vehicles can be combined as desired (e.g., in a preferred or customized ratio) prior to administration to the subject as a single administration, or can be administered separately, by different routes of administration and/or at different times.

The present technology can be further summarized by the following features:

1. A pharmaceutical formulation comprising:
   a first nanoparticulate delivery vehicle comprising a first active agent; and
   a second nanoparticulate delivery vehicle comprising a second active agent;
   wherein the first and second delivery vehicles are configured for coordinated delivery of the first and second active agents when the formulation is administered to a subject in need thereof.
2. The pharmaceutical formulation of feature 1, wherein the first and second nanoparticulate delivery vehicles are independently selected from the group consisting of polymeric nanoparticles, metallic nanoparticles, liposomes, micelles, and solid lipid nanoparticles.
3. The pharmaceutical formulation of feature 1, wherein the first and second delivery vehicles each have a zeta potential, and the zeta potential of the first nanoparticulate delivery vehicle and the zeta potential of the second nanoparticulate delivery vehicle differ by not more than about 15 mV; and
   wherein the first nanoparticulate delivery vehicle and the second nanoparticulate delivery vehicle each have a zeta potential in the range from about +15 mV to about +60 mV;
   or wherein the first nanoparticulate delivery vehicle and the second nanoparticulate delivery vehicle each have a zeta potential in the range from about −15 mV to about −60 mV;
   or wherein the first nanoparticulate delivery vehicle and the second nanoparticulate delivery vehicle each have a zeta potential in the range from about −15 mV to about +15 mV.
4. The pharmaceutical formulation of feature 1 which is a liquid suspension of said nanoparticulate delivery vehicles.
5. The pharmaceutical formulation of feature 1 which is a solid composition comprising said nanoparticulate delivery vehicles embedded in a biodegradable polymer matrix.
6. The pharmaceutical formulation of feature 1, wherein the first nanoparticulate delivery vehicle and the second nanoparticulate delivery vehicle each have an average diameter in the range from about 10 nm to about 900 nm.
7. The pharmaceutical formulation of feature 6, wherein the average diameters of the first and second nanoparticulate delivery vehicles do not increase more than 10% upon storage for 24 hours at a temperature in the range from about 4° C. to about 20° C. after they are mixed to produce the formulation.
8. The pharmaceutical formulation of feature 1, wherein the first nanoparticulate delivery vehicle and the the second nanoparticulate delivery vehicle each comprise poly(D,L-lactide-co-glycolide), (PLGA), mPEG-PLGA, 1, 2-dipalmitoyl-sn-glycero-3-phosphocholine (DPPC), 1,2-dioleoyl-3-tri methyl-ammonium-propane (DOTAP), poly-beta-amino-ester, cholesterol, polyacrylate, 1,2-distearoyl-sn-glycero-3 phosphoethanolamine-N-[methoxy(polyethyleneglycol)-2000 (DSPE-PEG2000), a metal, a metal alloy, poly(ethyl-ene-glycol), or a combination thereof.
9. The pharmaceutical formulation of feature 1, wherein the first and second active agents are independently selected from the group consisting of dactolisib, idelalisib, buparlisib, rapamycin, everolimus, temsirolimus, berzosertib, wortmannin, olaparib, veliparib, rucaparib, niraparib, talazoparib, alisertib, tozazertib, barasertib, danusertib, ruxolitinib, tofacitinib, debratinib, sorafenib, sunitinib, cabozantinib, foretinib, erlotinib, gefitinib, lapatinib, afatinib, neratinib, canertinib, navitoclax, obatoclax, venetoclax, pomalidomide, necrostatin, selumetinib, trametinib, pimasertib, palbociclib, roscovitine, dinaciclib, flavopiridol, galunisertib, adavosertib, antiviral agents, antibodies, Fc fusion proteins, anticoagulants, blood factors, bone morphogenetic proteins, engineered protein scaffolds, enzymes, growth factors, hormones, interferons, interleukins, thrombolytics, DNA constructs, or RNA constructs, mRNA, siRNA, and shRNA, and
   wherein the first and second active agents have different mechanisms of action or are selected from different classes of active agents.
10. The pharmaceutical formulation of feature 1, wherein the formulation has a greater therapeutic index, longer duration of action, longer serum half-life, higher solubility, greater therapeutic efficacy, reduced toxicity, reduced side effects, or reduced degradation compared to the free first and second active agents, administered singly or combined without their respective nanoparticulate delivery vehicles.
11. The pharmaceutical formulation of feature 1, wherein the proportion of the first nanoparticulate delivery vehicle to the second nanoparticulate delivery vehicle is in the range from about 100:1 to about 1:100 on a weight or molar basis for the first and second active agents.
12. A method of treating a disease or medical condition, the method comprising administering the pharmaceutical formulation of feature 1 to a subject in need thereof.
13. The method of feature 12, whereby a greater therapeutic index, longer duration of action, longer serum half-life, higher solubility, greater therapeutic efficacy, reduced toxicity, reduced side effects, or reduced degradation of the first or second therapeutic agent is achieved compared to administration of the free first and second active agents, singly or combined, without their respective nanoparticulate delivery vehicles.
14. The method of feature 12, wherein the disease or medical condition is selected from the group consisting of cancer, cardiovascular diseases, viral infections, bacterial infections, and traumatic brain injuries.
15. The method of feature 14, wherein the viral infection is COVID-19 or HIV/AIDS.
16. A pharmaceutical kit comprising:
   a first nanoparticulate delivery vehicle comprising a first active agent; and
   a second nanoparticulate delivery vehicle comprising a second active agent;
   wherein the first and second delivery vehicles are configured for coordinated delivery of the first and second active agents when the first and second delivery vehicles are administered to a subject in need thereof, and wherein the first and second nanoparticulate delivery vehicles are provided in separate containers.
17. A method of treating a disease or medical condition, the method comprising administering the first and second nanoparticulate delivery vehicles of the pharmaceutical kit of feature 16 to a subject in need thereof.
18. The method of feature 17, wherein the first and second delivery vehicles are premixed prior to administering at a ratio from about 100:1 (first vehicle:second vehicle) to about 1:100 on a weight or molar basis for the first and second active agents.

19. The method of feature 17, wherein the first and second delivery vehicles are administered separately in amounts or at times selected to provide said coordinated delivery.

20. The method of feature 17, wherein said coordinated delivery provides a greater therapeutic index, longer duration of action, longer serum half-life, higher solubility, greater therapeutic efficacy, reduced toxicity, reduced side effects, or reduced degradation of the first or second therapeutic agent is achieved compared to administration of the free first and second active agents, singly or combined, without their respective nanoparticulate delivery vehicles.

21. The method of feature 17, wherein the disease or medical condition is selected from the group consisting of cancer, cardiovascular diseases, viral infections, bacterial infections, and traumatic brain injuries.

22. The method of feature 21, wherein the viral infection is COVID-19 or HIV/AIDS.

23. An antiviral nanoparticulate therapeutic agent, comprising:
 a nanoparticulate delivery vehicle;
 one or more antiviral agents associated with the nanoparticulate delivery vehicle; and
 a virus targeting agent bound to an outer surface of the nanoparticulate delivery vehicle.

24. The antiviral nanoparticulate therapeutic agent of feature 23, wherein the delivery vehicle is selected from the group consisting of polymeric nanoparticles, metallic nanoparticles, liposomes, micelles, and solid lipid nanoparticles.

25. The antiviral nanoparticulate therapeutic agent of feature 23, wherein the virus targeting agent is an antibody or aptamer that binds to a virus surface protein promoting entry into a host cell of the virus.

26. The antiviral nanoparticulate therapeutic agent of feature 23, wherein the targeted virus is SARS-CoV-2 or HIV.

27. A method to aid in treating a viral infection, the method comprising administering the antiviral nanoparticulate therapeutic agent of feature 23 to a subject who is infected with the virus targeted by the virus targeting agent, whereby virus entry into cells of the subject is inhibited or replication of virus in the subject is inhibited.

As used herein, the term "average diameter" refers to the average diameter of particles measured utilizing dynamic light scattering (DLS), which is typically the mean value from the intensity distribution (called the Z average) and the polydispersity index (PDI) to describe the distribution width. The intensity weighted distribution can be converted to a volume weighted distribution if the refractive index of the sample is known, and the conversion is typically done using software with a particle size instrument. As such, the term "average diameter" herein can refer to a volume weighted particle size distribution with the volume weighting used to calculate the average, or other weightings can be used, such as intensity, surface area, or number distribution. No matter how the particle size distribution is weighted, the D50 refers to the size that splits the distribution with half above and half below the diameter of the median particle size. The term D50 can be used interchangeably with the term "median diameter" herein because the setting of particle size specifications is typically dependent upon the instrument or method used to measure particle size, which determines the weighting used to calculate the mean. To calculate an average diameter or a D50, the variable used to weight the average or the median can be determined by the particle size instrument used. For example, laser diffraction typically provides a volume weighting. Image analysis typically can provide a numerical or volume weighting. After the mean or median is weighted to a distribution, the D50 can be the average or the value that splits the distribution. Aside from DLS, tunable resistive pulse sensing (TRPS) can be used to measure average particle size and/or zeta potential. TRPS can provide a volume weighted average particle size distribution with high accuracy. The volume weighted size distribution can be used to calculate average size distribution or D50 as described above.

As used herein, the term "nanococktail" refers to a formulation containing two or more nanoparticulate delivery vehicles.

As used herein, the term "responsive analyte" refers to a substance that exhibits a measurable response upon contact with and/or exposure to one or more environmental stimuli. For example, the responsive analyte may provide a measurable response upon contact with and/or exposure to one or more environmental stimuli including an electromagnetic field or light. A responsive analyte may respond to biodegradation or temperature. A nanoparticulate delivery vehicle described herein can include a responsive analyte. An implant for administration of one or more nanoparticulate delivery vehicles can contain a responsive analyte associated with the implant. The responsive analyte can be bound, covalently or ionically, to the implant. The responsive analyte can be contained in the implant by steric or van der waals forces. When utilized with an implant for administration of one or more nanoparticulate delivery vehicles, a responsive analyte can aid in a time release of one or nanoparticulate delivery vehicles.

As used herein, the term "therapeutic index" or "therapeutic window" refers to the window or difference between the amount, concentration, or dose that gives an effective, desired pharmacological outcome and the amount, concentration, or dose that results in more adverse effects than the desired effects. An active agent with a small therapeutic window must be administered with care and control, e.g., by frequently measuring blood concentration of the drug, since it easily loses effects or gives acute adverse effects. The nanoparticulate delivery vehicles described herein can change, and be used to optimize, the therapeutic window of an active agent, for example, by changing serum half-life, by increasing the duration of action, by increasing solubility, or by decreasing toxicity. The therapeutic window of an active agent can change depending upon route of administration. The therapeutic window used herein can include one or more than one dose. The overlap between the therapeutic window of one active agent and another active agent can determine the combined effectiveness of the two active agents when administered together. The nanoparticulate delivery vehicles described herein can substantially increase the overlap between the therapeutic window of one active agent and another active agent, both with nanoparticulate delivery vehicles, as compared to the overlap in therapeutic windows of the same active agents when administered without the nanoparticulate delivery vehicles, i.e., as one "free" or individual active agent and another free or individual active agent. A "free" active agent in this context can include standard formulation ingredients, but it has been formulated for individual administration, not co-administration. A method of designing a nanoparticulate delivery vehicle can include a comparison of one or more variables, or a matrix of variables (e.g., duration of action, serum-half life, solubility, toxicity) associated with two or more active agents with nanoparticulate delivery vehicles and two or more free active agents without nanoparticulate delivery vehicles. The present technology allows specific design of therapeutic windows of two or more active agents for use in combination. As used herein, an "optimum combination index" refers to an optimum combination of therapeutic windows.

As used herein, the "duration of action" of an active agent is the length of time that the active agent is effective, for example, to provide a therapeutic window or to provide one or more effects for a patient. Duration of action can be a function of several parameters, for example, including serum (or plasma) half-life, the time to equilibrate between plasma and target compartments, toxicity, and the off rate of the drug from its biological target.

Metals suitable for metal or metal alloy nanoparticulate delivery vehicles include any metal suitable for administration to a subject including iron, gold, palladium, platinum, silver, copper, zinc, calcium, or compounds containing any of these metals. In some cases, a toxic metal can be provided with a coating that prevents toxicity, for example, when a metal nanoparticle is used for imaging. Examples of transition metals for use in the present technology include scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, ununnilium, unununium, and ununbium. As used herein, examples of metalloids include boron, silicon, germanium, arsenic, antimony, tellurium, polonium, selenium, and astatine.

As used herein, the terms "nanoparticle" and "nanoparticulate delivery vehicle" refer to a structure having at least one dimension on the nanoscale, that is, at least one dimension between about 1 and 1000 nm. The shape of the nanoparticles is not limited. The nanoparticulate delivery vehicles can include silica nanoparticles, clay (e.g., montmorillonite), carbon nanoparticles of any carbon form (e.g., fullerenes), mesoporous or nonporous methacrylate-functionalized silica, zirconium nanoparticles, biopolymers, protein(s), polysaccharide(s), poly-beta-amino-esters, polymeric nanoparticles, metallic nanoparticles, liposomes, micelles, epoxy, solid lipid particles and can include (e.g., oxides, hydroxides, sulfides, phosphates, fluorides, and chlorides) ceramics (e.g., inorganic nonmetallic solids). Nanoparticulate delivery vehicles can be in amorphous, polycrystalline, dense, porous, or hollow forms. Coatings, layers, or functionalization can be used. For example, an epoxy functionalization can be used to tune a zeta potential for some silica nanoparticles. A charged molecule, peptide, amino acid, or oligopeptide can be added to tune zeta potential (e.g., adsorbed protamine). The nanoparticulate delivery vehicles can have a core-shell structure or can have a homogeneous composition from surface to core.

A suspension comprising two or more nanoparticulate delivery vehicles can be a suspension in a liquid, a suspension in a gas, a suspension in a solid, or a solid (nanoparticulate) combination of the two or more nanoparticulate delivery vehicles. The gas is not limited and can be, for example, air, a hydrofluoroalkane (HFA), a propellant for dispersing nanoparticles for inhalation, 1,1,1,2-tetrafluoroethane, 1,1,1,2,3,3,3-heptafluoropropane, or an inert gas including hydrogen, helium, argon, xenon, or radon. The liquids are not limited and can be a liquid suitable for pharmaceutical administration to a subject including, for example, salts, pH modifiers, buffers, thickeners, preservatives, and surfactants. A solid suspension can include a tablet formulation, a capsule formulation, a powder, or a formed solid for use as an implant.

As used herein, the term "about" and "approximately" are defined to be within plus or minus 10%, 5%, 1%, or 0.5%.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with the alternative expression "consisting of" or "consisting essentially of".

BRIEF DESCRIPTION OF THE DRAWINGS

FIG. 7A presents the TLZ levels (ng/mL) found in plasma after a single dose, resulting a terminal half-life of 37.5 hours. FIG. 7B presents the DCB levels (μg/mL) in the plasma after a single dose, resulting in a half-life of 30.7 hours.

FIG. 8A shows nanoDCB starts to downregulate Rad51 in a tumor within 5 minutes of administration, and stably disrupts Rad51 for up to 24 hours. FIG. 8B shows tumor PAR levels and demonstrates nanoTLZ begins acting in a tumor within 30 minutes of administration and stably depleted PAR levels for at least 8 hours.

FIG. 11A illustrates blocking of virus mimicking particles (NanoCOV) into cells by AntiCoVNP using antibody and drug inhibitors.

DETAILED DESCRIPTION

The present technology provides nanoparticulate delivery vehicles that can be individually designed using strategies described herein; each such delivery vehicle contains one or more active agents. The nanoparticulate delivery vehicles can be designed to provide coordinated delivery of the active agents when administered to a subject. Coordinated delivery can take many forms, each of which offers at least one advantage over combined administration of formulations that are not designed or even intended for co-administration with another agent. For example, coordinated delivery can maximize overlap between the therapeutic windows of two or more active agents by comparing a matrix of variables between the free active agents and the active agents with the nanoparticulate delivery vehicles. The nanoparticulate delivery vehicles may be functionalized with one or more responsive analytes. The nanoparticulate delivery vehicles may include a targeting moiety. The nanoparticulate delivery vehicles can be, for example, polymeric nanoparticles, metallic nanoparticles, liposomes, micelles, or solid lipid particles.

The technology can provide a cocktail of two or more nanoparticulate delivery vehicles, or a "nanococktail". For example, two, three, four, five, or more different nanoparticulate delivery vehicles can be combined into a single nanococktail. The nanococktail allows for tailored dosing, as the concentration of a single active agent can be decreased while independently maintaining the concentration of the other active agent(s). In the nanococktail, the concentration of one active agent can be changed by changing the amount of the nanoparticulate delivery vehicle including that active agent. The nanoparticulate delivery vehicles can be provided in any ratio in the nanococktail. If toxicity is observed, the dose of non-toxic active agents need not be decreased because they are administered in a single system. The dose or pharmacokinetics of the active agent that has the toxicity can be changed without changing the dose or pharmacokinetics of the others. The nanococktail bypasses the limitation of administering active agents in a fixed ratio or with fixed pharmacokinetics.

Figure 1A:
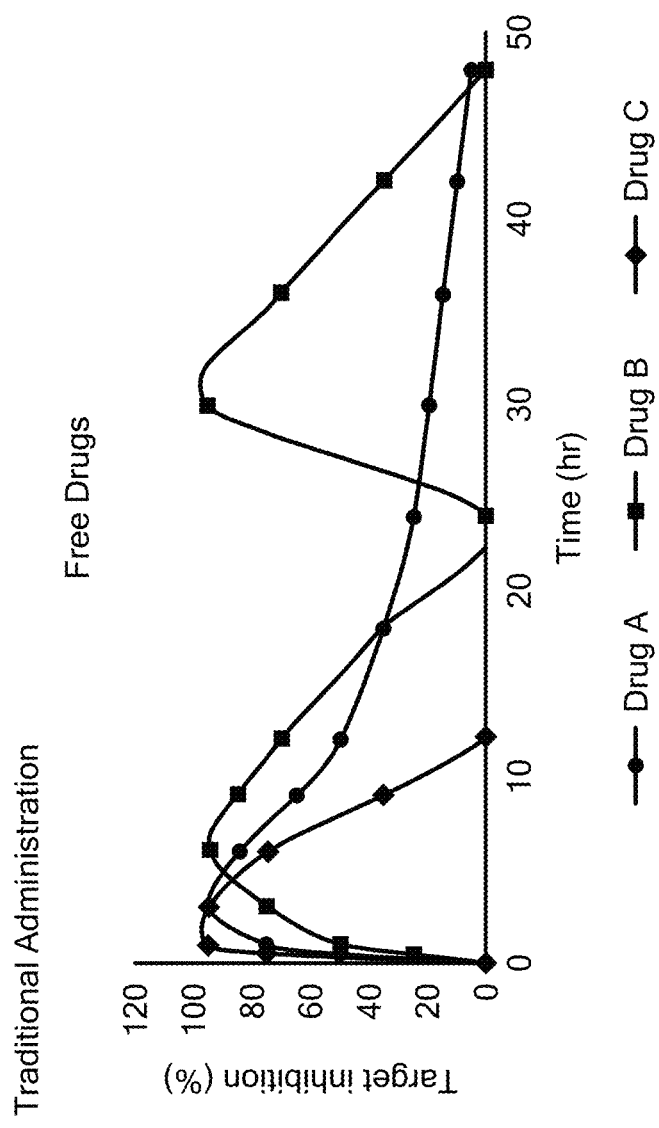
FIG. 1A shows a plot of pharmacokinetics (time v. target % inhibition) after non-nanoparticulate (traditional) administration of Drug A, Drug B, and Drug C each as single formulated agents.
Figure 1A:
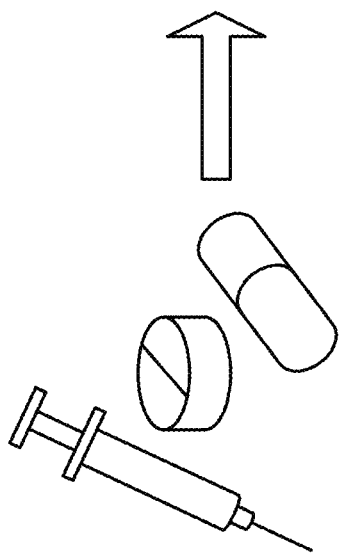
Figure 1B:
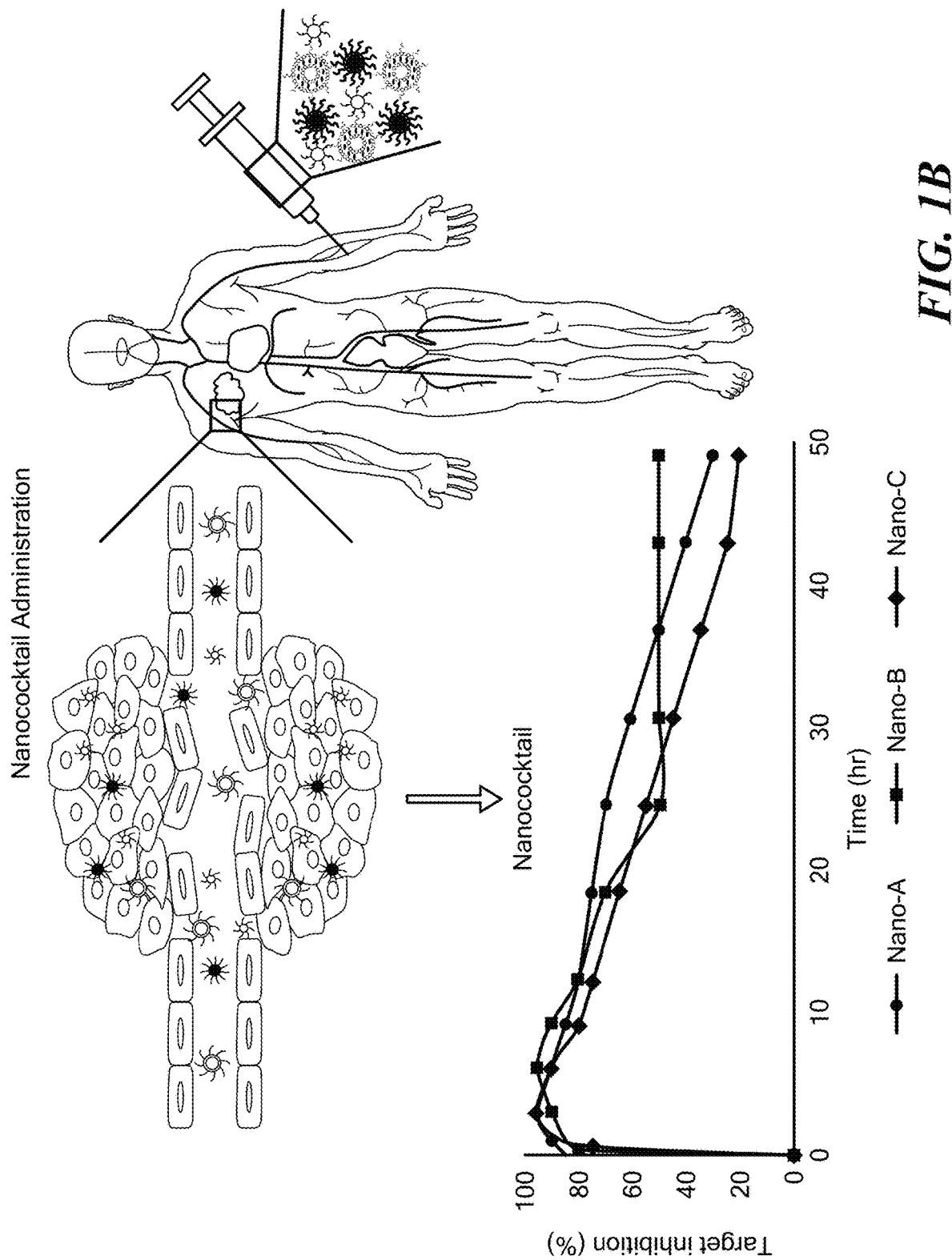
FIG. 1B shows a plot of pharmacokinetics (time v. target % inhibition) upon simultaneous administration of Drug A, Drug B, and Drug C in a nanococktail containing a stable nanoparticulate suspension of all formulations.

The nanococktail is a mixture of nanoparticulate delivery vehicles, each engineered to optimally deliver a single active agent. The mixture of two or more different nanoparticulate delivery vehicles is engineered such that they can be titrated to achieve the optimal dose or exposure in a single nanococktail suspension. The nanoparticulate delivery vehicles in the cocktail are further designed such that they maintain stability in the mixture. FIG. 1A illustrates the limitations of pharmacokinetics (time v. target % inhibition) upon traditional administration of Drug A, Drug B, and Drug C each as single free formulated (without nanoparticulate delivery vehicles) agents. The free drugs have different pharmacokinetic profiles over time. FIG. 1B shows a plot of pharmacokinetics (time v. target % inhibition) upon simultaneous administration of Drug A, Drug B, and Drug C in a nanococktail containing a stable nanoparticulate suspension of all nanoparticulate delivery vehicles. In FIG. 1B, the pharmacokinetics of the three active agents (drugs) are similar, illustrating a capability of the nanococktails provided herein. Duration of action of Drug A, Drug B, and Drug C can be nearly equal. Therapeutic windows for Drug A, Drug B, and Drug C can be provided with maximum overlap to a specific patient.

For example, a nanococktail may include a polymeric nanoparticulate delivery vehicle mixed with a liposomal nanoparticulate delivery vehicle, two different polymeric formulations, a solid lipid and liposomal formulation, a liposomal formulation and a metallic nanoparticulate delivery vehicle, or a micelle formulation with a polymeric formulation, mixed together in a nanococktail. The nanococktail may include other ingredients, for example, stabilizers, pH modifiers, excipients, osmolality adjusters (e.g., a salt), and other active agents. For IV administration, osmolality adjusters may be critical. For oral administration, drug in capsule may suffice or excipients can be added. For administration by inhalation, the nanoparticulate delivery vehicles can be provided in an inhaler that can combine a variable or set ratio of two or more nanoparticulate delivery vehicles. For administration by a topical skin formulation or a skin patch, a gel or other formulation ingredients can be included.

Administration of one or more nanoparticulate delivery vehicles can be accomplished by implanting one or more sustained delivery polymer implants in a subject's body or sustained delivery skin patches mounted on the skin of a subject. The polymer implant(s) can release or deliver one or more nanoparticulate delivery vehicles including therapeutics or vaccines over a time period in the range from about one week to several months or longer. Any of the nanoparticulate delivery vehicles herein can be contained or embedded in a biodegradable polymer matrix, for sustained release. Biodegradable polymers can be polymers which decompose or dissolve as a result of the action of movement, bodily conditions, hydrolytic cleavage, microorganisms, enzymes, or feedback to a stimulus, and these polymers may include ester, amide, disulfide, or ether bonds. Examples of biodegradable polymer matrices are poly β-hydroxybutyrate-co-β-hydroxy valerate (PHBV); nylon 2-nylon 6, which is a polyamide copolymerization of glycine ($H_2N$—$CH_2$—COOH) and aminocaproic acid ($H_2N$—$(CH_2)_5$—COOH); polyhydroxybutyrate (PHB), which can be formed by the condensation of hydroxybutyric acid (3-hydroxy butanoic acid) with copolymers of glycolide with caprolactone, lactide or trimethylene carbonate; polylactides such as PLLA, PDLLA, or any combination; poly(lactide-co-glycolide) (PLGA); polycaprolactone (PCL); poly(butylene succinate) (PBS) and its copolymers, poly(p-dioxanone)

(PPDO); and poly[oligo(tetramethylene succinate)-co(tetramethylene carbonate)] (PEC). A method to convert polyolefins to biodegradable polymers can include the introduction of antioxidants into the polymer chains. Antioxidants can react under biological conditions or UV, inducing degradation by photo-oxidation. Other suitable materials include starch, cellulose, and polyesters. Any of the biodegradable polymers can be utilized to synthesize one or more of the nanoparticulate delivery vehicles disclosed herein. An implant can be responsive, for example, to temperature, applied electromagnetic radiation, applied sonic waves, serum concentration of one or more active agents, and serum concentration of toxins.

Metallic nanoparticles can be synthesized, for example, by forming a first solution including a metal or metal alloy and precipitating the metal from the solution. The solution can include an active agent, or the active agent can be added to the nanoparticles after formation. The metal or metal alloy can include a transition metal, a metalloid, or any suitable metal. The solution can be heated and cooled during or before precipitation and may include one or more ligands. Other techniques include and are not limited by mechanical milling, sol-gel processes, nanosphere lithography, chemical, photochemical, electrochemical, and sonochemical, templating, thermal reduction, photolithography, laser ablation, biogenic synthesis, and electron beam lithography approaches. After formation, the nanoparticles can be isolated by, for example, centrifugation, filtration, magnetic properties, sedimentation, or agglomeration. One or more treatment steps can be applied after formation of the nanoparticles, for example, homogenizing, planetary or zirconium grinding to refine particle size or to bind an active agent to the nanoparticles. The metal nanoparticles can be partially or fully coated after formation, for example, by polymer, lipid, surfactant, another metal or alloy, a responsive analyte, or a targeting moiety. Examples of metals that can be used for metallic nanoparticles are iron, copper, selenium, gold, platinum, silver, titanium, zinc, cerium, and thallium or their compounds (e.g., oxides, hydroxides, sulfides, phosphates, fluorides, and chlorides) or alloys thereof with or without compounds of the metals or alloys. A crystalline or amorphous structure of the metallic or alloy nanoparticles can be determined by synthesis or by post processing.

Figure 2:
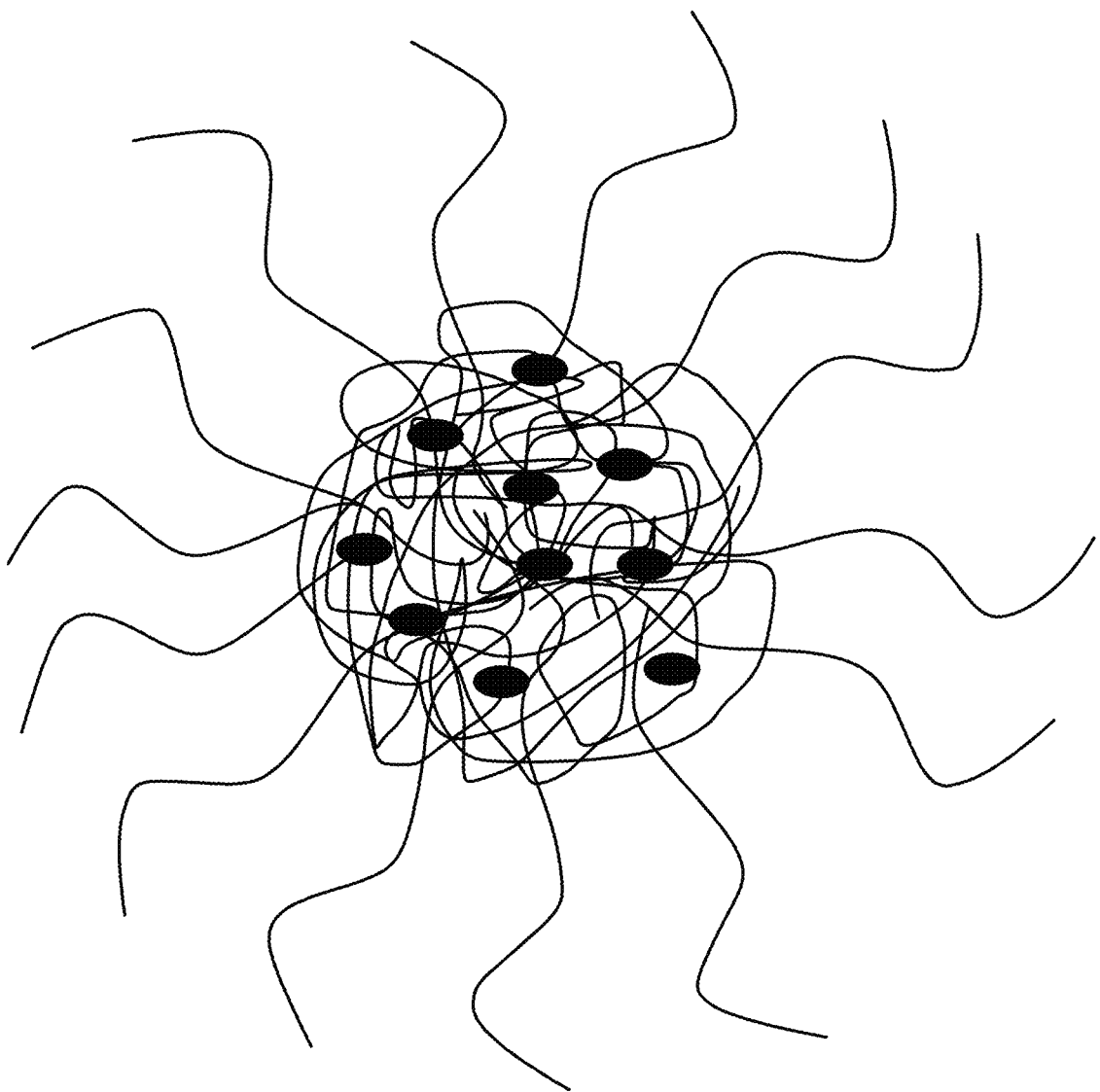
FIG. 2 is a schematic of a polymeric formulation in which a pharmaceutical agent (active agent) is encapsulated within the polymeric core of the nanoparticle. The polymeric formulation becomes part of the nanococktail.
Figure 3A:
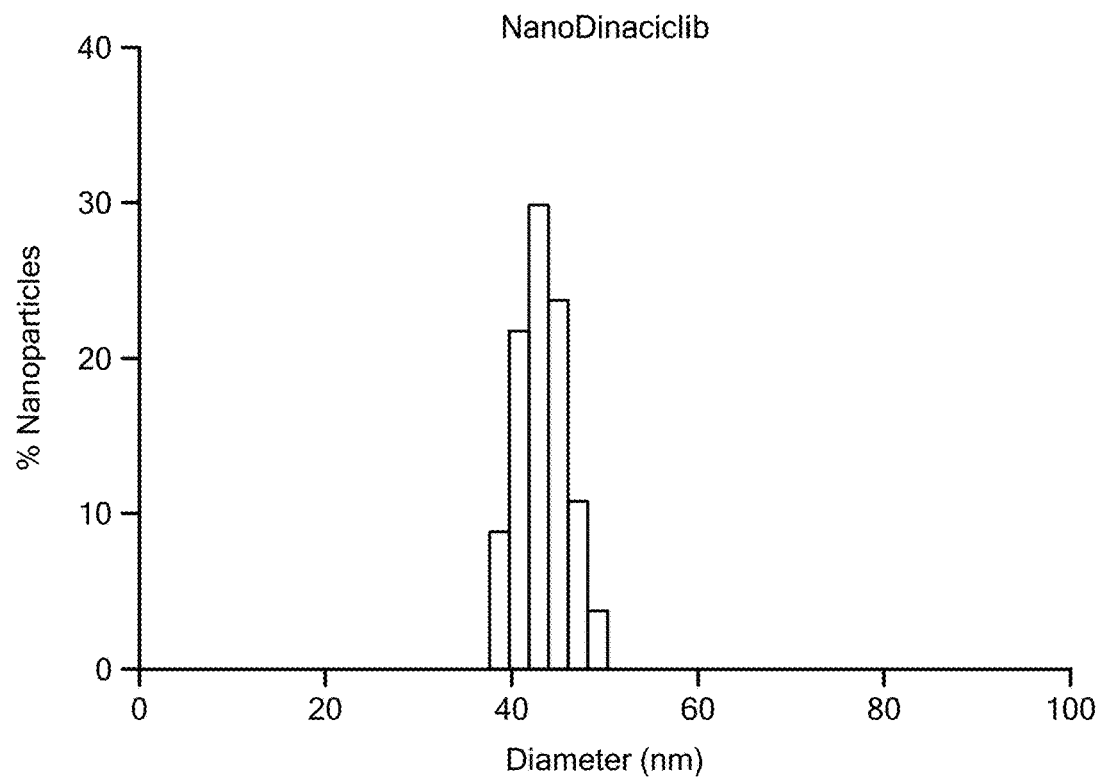
FIG. 3A shows dynamic light scattering (DLS) characterization of a nanoformulation of dinaciclib (nanodinaciclib, nDCB).

Polymer nanoparticles may be synthesized, for example, by forming a solution containing one or more polymers in a suitable solvent or mixture of solvents. An active agent can be dissolved in the same solvent or provided in a separate solution. Nanoparticles can be formed using nanoprecipitation from the solution. The nanoparticles can be formed with the active agent, encapsulating the active agent within the nanoparticles, as is illustrated in FIG. 2. Alternatively, the active agent can be added after formation of the nanoparticles. One or more treatment steps can be applied after formation of the nanoparticles, for example, isolation, purification, coating, or homogenizing to refine particle size or to bind the active agent to the nanoparticles. The suitable solvent and any unencapsulated or unbound free drug molecules can be removed by washing the nanoparticles, for example, one or more times in a centrifuge tube, using a solvent wash, or utilizing a suspension step. The nanoparticles can then be stored or resuspended in a suitable solvent for formulation in a nanococktail. An example of DLS size distribution of polymer nanoparticulate delivery vehicles is shown in FIG. 3A. Polymer nanoparticles are shown in the transmission electron micrograph of FIG. 3B.

Figure 4A:
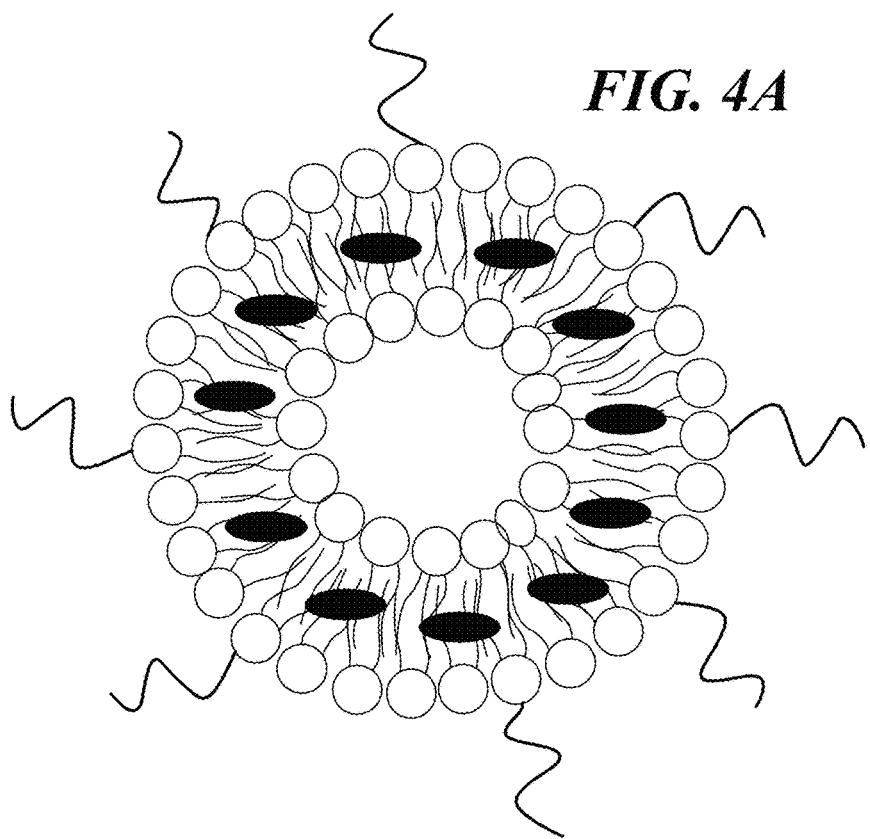
FIG. 4A is a schematic of a liposomal formulation in which a pharmaceutical agent (active agent) is encapsulated within the lipid bilayer. The liposomal formulation becomes part of the nanococktail.

Lipid nanoparticles may be synthesized, for example, by forming a solution containing one or more lipids in a suitable solvent or mixture of solvents with or without surfactants, stabilizers, or other compounds. An active agent can be provided in solid form, dissolved in the same solvent, or provided in a separate solution. Lipid nanoparticles can be formed using homogenization of the active agent with the solution of lipids. The lipid nanoparticles may be formed and isolated without the active agent, and the active agent can be incorporated in the lipid nanoparticles by mixing or homogenizing the active agent, in solid or solution form, with the lipid nanoparticles in a suspension. The nanoparticles can be formed with the active agent, encapsulating the active agent within the nanoparticles, as is illustrated in FIG. 4A. One or more treatment steps can be applied after formation of the nanoparticles, for example, to refine particle size or to bind the active agent to the nanoparticles. The suitable solvent and any unencapsulated or unbound free drug molecules can be removed by washing the nanoparticles, for example, one or more times in a centrifuge tube or by lyophilization. The nanoparticles can then be stored or resuspended in a suitable solvent for formulation in a nanococktail. Lipid nanoparticles are shown in the transmission electron micrograph of FIG. 4B. Micelles may be formed by a process similar to that of lipid nanoparticles or liposomes when the concentration of a surfactant, in the synthesis medium, is greater than the critical micelle concentration, and the temperature of the system is greater than the critical micelle temperature, or Krafft temperature. Any of the methods of forming nanoparticles or nanoparticulate vehicles herein can include the formation or the addition of free radicals by any means known in the art.

Any of the methods for making nanoparticles or nanoparticulate delivery vehicles can include additional steps or additives. For example, salting-out, dialysis, exposure to supercritical fluid (e.g., $CO_2$), solvent evaporation, lyophilization, sudden pressure or vacuum exposure, exposure to plasma or ions, micro-emulsion, interfacial polymerization. Homogenizing can be accomplished by any means known in the art. Examples are forcing the suspension at high pressure through small holes, blending, bead milling, ultrasonic treatment (also sonication), rotor-stator mechanical, high pressure, and other physical forces such as extruders, hammermills, and colloid mills.

A responsive analyte can be added to the nanoparticulate delivery vehicles during synthesis or after. Examples of responsive analytes are compounds that change bonds or conformation upon exposure to electromagnetic radiation, UV-light (conjugated vinyl bonds), temperature, or sonic waves. Responsive analytes can be utilized to release active agents from one or more of the nanoparticulate delivery vehicles after administration to a subject. For example, two or more nanoparticulate delivery vehicles can be administered subcutaneously. Sonication can be applied to the two or more nanoparticulate delivery vehicles through the epidermis. UV light can interact with the two or more nanoparticulate delivery vehicles through the epidermis. The two or more nanoparticulate delivery vehicles can provide a signal visible through the epidermis, for example, to indicate pressure, temperature, active agent release, or to indicate movement. The signal can be detectable outside of visible electromagnetic radiation, for example for imaging. Responsive analytes can be used, for example, for imaging a nanoparticulate delivery vehicle within a subject. For example, one or more metal ions can be included in the polymer or lipid nanoparticulate delivery vehicles to enhance response for imaging. Other examples of responsive analytes are compounds that release active agents at body temperature (about 37° C.) but not at room temperature (about 20-25° C.). Responsive analytes may release an active agent after administration to a subject but not before.

The entire synthesis of nanoparticulate delivery vehicles can be self-assembling. The methods of making the nanoparticulate delivery vehicles may consist of a one-step synthetic strategy. For example, a synthetic strategy wherein at least a first reactant and a second reactant or a reaction agent are converted to a reaction product in a single synthesis step. For example, as described herein, the solution of metal (or alloy), polymer, or lipid may be converted to nanoparticulate delivery vehicles in a single synthesis step. Alternatively, the methods of making nanoparticulate delivery vehicles may include multiple steps to provide the nanoparticles. For example, additional steps can be included to further add responsive analytes, targeting moieties, shells, or coatings. The nanoparticulate delivery vehicles can be cured after formation by, for example, a heat annealing, a pH treatment, an exposure to UV light or to electromagnetic radiation, and one or more steps can be provided for sterilization such as irradiation or filtration.

The nanoparticulate delivery vehicles may include a core nanoparticle with a partial or complete shell on the core. In this example, the size of the nanoparticle includes the core and the shell. For example, the metal or alloy nanoparticles can be sputter coated to form a hard outer shell on the metal nanoparticles. The shell material may include a "soft shell" material. As used herein, "soft" refers to any nanoparticle coating forming material as described herein including a material capable of self-assembly. The soft shell can be self-assembled upon a nanoparticle core material. For example, the polymer or lipid syntheses described herein can be utilized with metal or alloy nanoparticles to form a soft shell of polymer or lipid on the metal nanoparticles. Examples of soft shell materials include, but are not limited to, poly-beta-amino-esters (PBAEs), surfactants, various polymers, a non-surfactant molecule having one or more specific functional groups, and a combination thereof. The shell material may include an organic material that includes at least one material capable of self-assembly. Examples of organic shell materials include, but are not limited to, organic soft shell materials such as organic surfactants, organic or organic molecule-containing polymers, non-surfactant organic molecules having one or more specific functional groups. The shell material can include antibodies, aptamers, radioisotopes, and dissolution modifying additives (e.g., methyl cellulose or polyvinylpyrrolidone), or these materials can be included in the core nanoparticle.

The nanoparticulate delivery vehicles may include nanopores. The nanopores can contain one or more active agents. The average size of the nanopores can be at the molecular scale, for example, from about 1 nm to about 10 nm. The nanopores can be filled, for example, with an active agent during synthesis, with a responsive analyte, with a zeta potential modifier, or an ion. At least a portion of the pores can be empty after synthesis of the nanoparticulate delivery vehicles, and this portion can be modified, filled, closed, or sealed during another subsequent step. The nanoparticulate delivery vehicles can include spikes, spike proteins, protrusions, decorating antibodies, oligonucleotides, glycopeptides, or a combination thereof.

A targeting moiety can be added to the nanoparticulate delivery vehicles during synthesis or after. Examples of targeting moieties are substances that accumulate at a tumor or other site within a subject. The targeting moiety can comprise an oligonucleotide or peptide molecule that bind to a specific target molecule. Targeting moieties can be utilized to release active agents from one or more of the nanoparticulate delivery vehicles in a specific location after administration to a subject. Targeting moieties can be used in combination with responsive analytes. For example, the targeting moiety can localize one or more nanoparticulate delivery vehicles to a specific location within a subject, then a responsive analyte can be utilized to release one or more active agents from the nanoparticulate delivery vehicles. In an example, a responsive analyte can release an active agent upon application of sonic waves to an area, application of electromagnetic waves to an area, or application of heat to an area. The application of heat may come from a change in temperature within a patient over time.

Any of the nanoparticulate delivery vehicles can include radioisotopes or compounds useful for imaging, application of heat (hyperthermia therapy), or for a specific treatment. For example, the metal or metal alloy nanoparticles can include magnetic properties by designing the partial or full crystalline structure to enable a high contrast for imaging.

Any of the nanoparticulate delivery vehicles can be biodegradable, meaning that the nanoparticulate delivery vehicles are absorbed by the metabolism during or after delivery of the active agent.

The nanococktail may include any combination of nanoparticulate delivery vehicles based on the number of active agents to be delivered. For example, the nanococktail may consist of two different nanoparticulate delivery vehicles, three different nanoparticulate delivery vehicles, four different nanoparticulate delivery vehicles, or five different nanoparticulate delivery vehicles or more.

The nanoparticulate delivery vehicles in the nanococktail may have an average diameter of about 10 nm, about 20 nm, 30 nm, about 40 nm, about 50 nm, about 60 nm, about 70 nm, about 80 nm, about 90 nm, about 100 nm, about 120 nm, about 150 nm, about 200 nm, about 250 nm, about 300 nm, about 400 nm, about 500 nm, about 600 nm, about 700 nm, about 800 nm, about 900 nm, or about 1000 nm. For example, the average diameter can be from about 10 nm to about 900 nm. In a suspension of nanoparticles a percentage may have a diameter as indicated above. For example, at least 50%, at least 60%, at least 70%, at least 80%, at least 90%, at least 95% of the nanoparticles may have the average diameters listed above.

The nanoparticulate delivery vehicles in the nanococktail may have a spherical or near spherical shape, a star shape, a rod shape, a nano-cage shape, a cube shape, a triangular shape, a porous (sponge-like) shape, a needle shape, and any shape dependent upon synthesis of the nanoparticulate delivery vehicles and by design. The nanoparticulate delivery vehicles can be soft or hard. The nanoparticulate delivery vehicles can be designed to traverse blood vessels into interstitial spaces or to remain inside blood vessels. The nanoparticulate delivery vehicles can be designed to target a specific location within a subject or to circulate throughout the bodily systems (e.g., cerebrospinal fluid, circulatory system, lymphatic system).

Each nanoparticulate delivery vehicle in the nanococktail is designed to meet the needs of the pharmaceutical agent to be delivered and to meet the needs of the treatment. Each nanoparticulate delivery vehicle will modify the pharmacokinetics and pharmacodynamics of the active agents such that co-administration will lead to the optimal therapeutic effect, maximum overlap of therapeutic windows, or maximum duration of action/benefit. For example, an active or pharmaceutical agent may be encapsulated to improve solubility. The active agent can be bound to the nanoparticulate delivery vehicle for example, through ionic or covalent bonding. A linker can be provided to link the active agent to the nanoparticulate delivery vehicle through ionic or covalent bond. The linker can be a responsive agent that responds to, for example, electromagnetic radiation, temperature, movement, or sonic waves. The linker can be a non-responsive agent that enhances bonding of an active agent to a nanoparticulate delivery vehicle through charge, hydrogen bonding, covalent bonding, or steric interaction, for example. A pharmaceutical agent with a short circulation half-life may be encapsulated to extend the half-life. A pharmaceutical agent may be encapsulated to generate an extended release profile. The pharmaceutical agent may be encapsulated to modify the distribution profile. An active (or pharmaceutical) agent can be encapsulated to protect from rapid degradation or to enhance solubility.

The nanoparticulate delivery vehicles must be engineered to exhibit similar zeta potentials such that charge does not induce aggregation upon mixing in a nanococktail. For example, all nanoparticulate delivery vehicles in the nanococktail must be cationic or all must be anionic. The nanoparticulate delivery vehicles may also be near neutral. The zeta potentials of cationic nanoparticulate delivery vehicles may range from +60 to +15 mV. The zeta potentials of anionic nanoparticulate delivery vehicles may range from −60 to −15 mV. The zeta potentials of neutral nanoparticulate delivery vehicles may range from −15 to +15 mV. The nanoparticulate delivery vehicles must be engineered such that the charge differential between the nanoparticulate delivery vehicles in the nanococktail is not more than 15 mV.

The nanoparticulate delivery vehicles in the nanococktail must be independently stabilized against aggregation by steric forces such as the addition of polymers or surfactants. The nanoparticulate delivery vehicles in the nanococktail should be stabilized using the same steric forces, for example all nanoparticulate delivery vehicles can be engrafted with poly(ethylene-glycol) to keep the nanococktail stable. Examples of surfactants are amphiphilic substances, anionic surfactants, nonionic surfactants, cationic surfactants, amphoteric or zwitterionic surfactants, and wetting agents. Two or more surfactants can be combined to inhibit aggregation.

The nanococktail may be used to treat any number of injuries, diseases or medical conditions where two or more pharmaceutical agents demonstrate enhanced efficacy. For example, the nanococktail may be used to treat cancer, a bacterial infection, COVID-19 or a viral infection, rheumatoid arthritis, or traumatic brain injury.

The nanoparticulate delivery vehicles in the nanococktail may deliver any pharmaceutical agent such as small molecule drugs. For example, the small molecule drug can be inhibitors such as, dactolisib, idelalisib, buparlisib, rapamycin, everolimus, temsirolimus, berzosertib, wortmannin, olaparib, veliparib, rucaparib, niraparib, talazoparib, alisertib, tozasertib, barasertib, danusertib, ruxolitinib, tofacitinib, debratinib, sorafenib, sunitinib, cabozantinib, foretinib, erlotinib, gefitinib, lapatinib, afatinib, neratinib, canertinib, navitoclax, obatoclax, venetoclax, pomalidomide, necrostatin, selumetinib, trametinib, pimasertib, palbociclib, roscovitine, dinaciclib, flavopiridol, galunisertib, or adavosertib. Large molecules, such as proteins and oligonucleotides can be delivered with the nanoparticulate delivery vehicles.

Encapsulation of an active agent in a nanoparticle delivery system that is water soluble provides an alternative delivery mechanism. Nanoparticle delivery systems can also be utilized to protect the cargo they encapsulate from degradation upon administration. Naked nucleic acids are rapidly degraded by nucleases upon administration. Therefore, in order to utilize nucleic acid based therapeutics, modifications to prevent degradation or delivery systems, such as nanoparticles, to mask the cargo from nuclease mediated degradation are essential. The nanoparticulate delivery vehicles in the nanococktail can deliver DNA or RNA based therapeutics. Biologic therapeutics may include, antibody-based drugs, Fc fusion proteins, anticoagulants, blood factors, bone morphogenetic proteins, engineered protein scaffolds, enzymes, growth factors, hormones, interferons, interleukins, thrombolytics, DNA constructs, or RNA constructs such as, mRNA, siRNA, or shRNA.

For example, in the treatment of cancer a traditional cytotoxic chemotherapeutic may be part of the nanococktail, while a targeted therapy may also be part of the nanococktail. Examples of active agents for cancer therapies are provided in Table 1. The nanococktail may also contain two or more targeted therapies or two or more chemotherapeutics. The nanoformulations in the nanococktail may contain a small molecule with one nanoparticulate delivery vehicle, while the other nanoparticulate delivery vehicle contains a biologic such as a protein or RNA-based therapeutic. One nanoparticulate delivery vehicle may include an active agent of one class (e.g., immunosuppressant), and another nanoparticulate delivery vehicle can contain an active agent of another class (e.g., topoisomerase inhibitor, topotecan). As used herein, a class of active agent refers to a known mechanism of action for an active agent. Examples of immunosuppressant are rapamycin, cyclosporine A, and prednisolone. An active agent may be a tubulin or microtubule inhibitor. Examples are paclitaxel are vincristine. Other examples of classes of active agent effective against cancer are a kinase inhibitor, a cyclin dependent kinase inhibitor, a polymerase inhibitor, and a poly ADP ribose polymerase inhibitor. For example, one nanoparticulate delivery vehicle can be utilized with one class of active agent that has a known free therapeutic window. A second nanoparticulate delivery vehicle can be utilized with a second class of active agent that has a second known, free therapeutic window. By utilizing a method of making a pharmaceutical formulation herein, the first nanoparticulate delivery vehicle can be designed to provide a different therapeutic window compared to the first active agent without the nanoparticulate delivery vehicle. The second nanoparticulate delivery vehicle can be designed to provide a different therapeutic window compared to the second active agent without the nanoparticulate delivery vehicle. The overlap between the therapeutic windows of the first active agent and the second active agent, with the nanoparticulate delivery vehicles, can be designed to minimize toxicity, to maximize overlapping durations of action, to maximize overlapping serum half-lives, to provide maximum pharmacodynamics, to maximize solubility, and to prevent degradation, for example.

TABLE 1

| Examples of Cancer Therapies | | |
|---|---|---|
| Doxorubicin | Altrazeal | G4H-Diab-Nano |
| Paclitaxel | Aminolevulinic Acid | Gemcitabine |
| Bupivacaine | Botulinum toxin A | GLPG0555 |
| Amphotericin B | Chitosan | HL-009 |
| Irinotecan | Cholesterol | Imiquimod |
| Vincristine | Glutathione | Interleukin 2 |
| Cytarabine | Gold | Iodixanol |
| Cytarabine: Daunorubicin | Iniparib (SAR240550-BSI-201) | Latanoprost |
| Silver | Iron | Lithium |

TABLE 1-continued

Examples of Cancer Therapies

| | | |
|---|---|---|
| Docetaxel | Kogenate FS | Lopinavir |
| Hydroxyapatite | Polyethylenimine | luteolin |
| Daunorubicin | Promitil | Megestrol acetate |
| NanoTab | Rhenium | Meglumine Antimoniate |
| Amikacin | SN38 | MnSOD |
| Curcumin | T4N5 | MPER-656 |
| Ferumoxytol | Tretinoin | MPLA |
| Mitoxantrone Hydrochloride | vitamin C and vitamin E | NDDP |
| Casein | 188Re-BMEDA | Oxaliplatin |
| Lurtotecan | 2-methoxyestradiol | OZ439 |
| Annamycin | 6-prenylnaringenin | Ozone |
| Cisplatin | Alendronate | Panobinostat |
| Fentanyl | Anthralin | Paromomycin |
| Rapamycin | Astaxanthin | PF-06260414 |
| Alprostadil | AZD4635 | Polyamidoamine |
| Cyclosporine A | BikDD | PRO-040201 |
| Lidocaine | Capsaicin | Prostaglandin |
| prednisolone | Ceramide | rFVIII-FS |
| Silver Fluoride | Cetirizine dihydrochloride | Sirolimus |
| Vinorelbine tartrate | Cetuximab | Titanium Dioxide |
| Nanoparticle MRI | Coenzyme Q10 | TKM-080301 |
| 9-Nitro-20 (S)-Camptothecin | CPT-11 | TLK199 HCl |
| Albumin | Diclofenac | Treprostinil (L606) |
| BPM31510 | DPX-0907 | Ubidecarenone |
| Carbon | Efavirenz | Urea |
| Topotecan | estradiol | Vineatrol |
| Zinc Oxide | Fluoride | |

A method of treating cancer, COVID-19, an injury, or any condition that can have an enhanced effect by combining two or more active agents can include combining one class of active agents with a second class of active agents. For example, a microtubule inhibitor on a first nanoparticulate delivery vehicle can be combined with a kinase inhibitor on a second nanoparticulate delivery vehicle.

The nanococktail suspension may be administered by a parenteral route. The parenteral route may be intravenous, intraperitoneal, subcutaneous, intramuscular, intraocular, or direct administration at or near the site of neovascularization. The nanococktail may also be administered by other routes including orally, topically, or intranasally. The nanococktail may be premixed for co-administration of the formulations. The nanococktail also may consist of sequential administration of the formulations such that one is administered directly after the other.

The nanoparticulate delivery vehicles can be combined in a pharmaceutical formulation (nanococktail) to provide a targeted matrix effect for delivery of a combination therapy (a nanococktail) to a patient. The technology can provide methods of treating a patient that will minimize tolerability or side effects while maximizing delivery of one or more active agents to a targeted area. The methods can be referred to as maximizing the overlap between therapeutic windows of two or more active agents. The technology can provide methods of making nanoparticulate pharmaceutical formulations that further provide the caregiver options to titrate and to tailor the formulation just before administration to a specific patient. The technology enables a caregiver to take into consideration a matrix of variables (e.g., patient conditions, degradation, serum half-life, targeting, toxicity) before administering two or more active agents to a patient, thereby giving the caregiver pre-planned control over the active agents, even after administration to the patient.

In some examples, the nanococktail contains the active agents in ratios from about 1:1 to 1:10 (active agent:non-active agent w:w). However, the technology can provide much smaller amounts of active agent to non-active agent, for example, when a highly potent active agent is encapsulated, bound, or incorporated with the nanoparticulate delivery vehicles.

The technology includes a method of treating a disease or condition, the method including administering to a subject in thereof a nanococktail, the nanococktail including: two or more distinct nanoparticulate delivery vehicles carrying distinct therapeutics. The disease or condition is not limited and, for example, can be cancer, infections such as HIV/AIDS, cardiovascular disease, COVID-19 or viral infection, bacterial infections, acute automobile or combat injuries, or traumatic brain injuries. For example, a dry formulation of the nanoparticulate delivery vehicles can be provided for application to acute injuries.

Figure 9A:
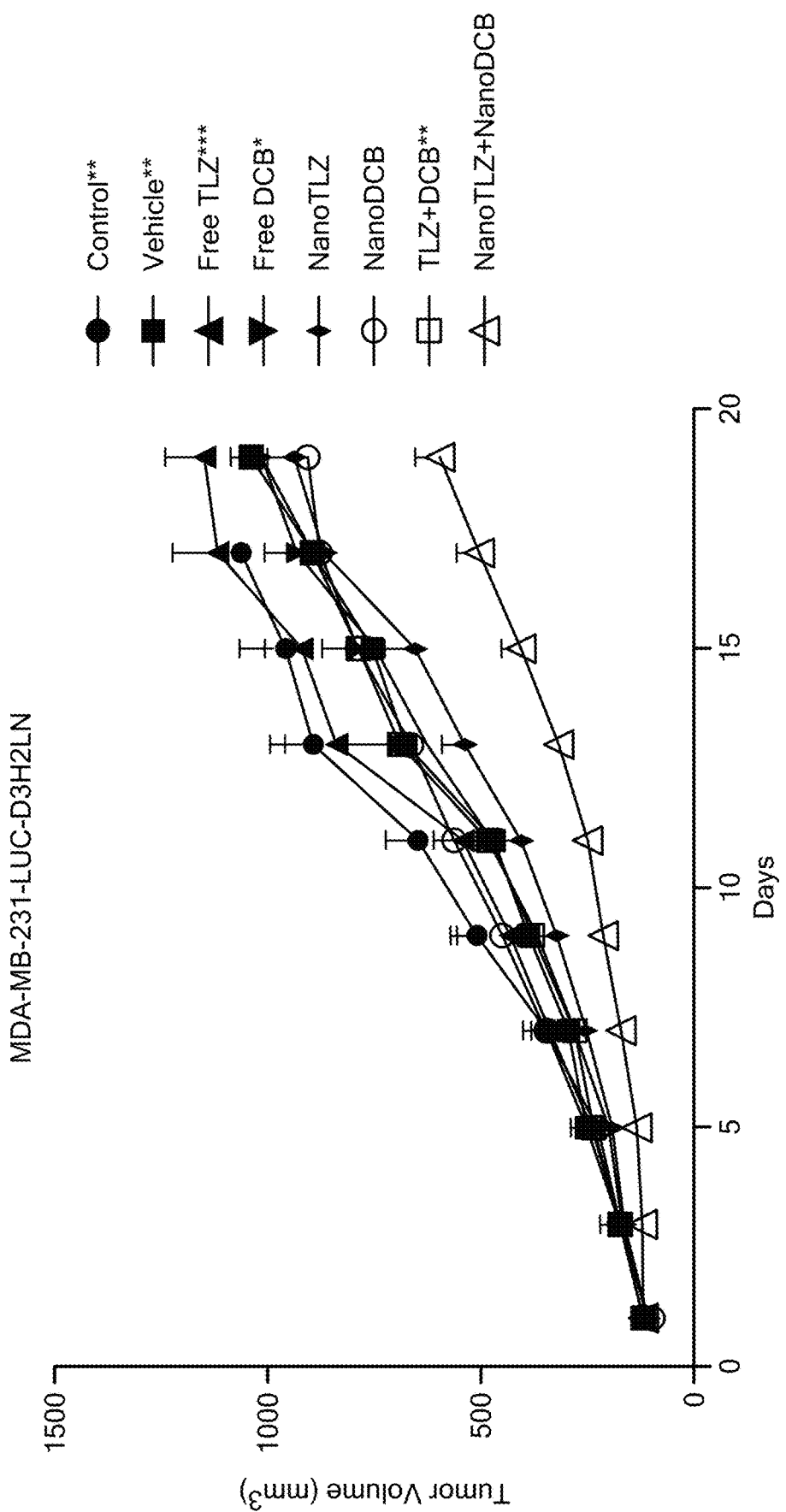
FIG. 9A shows tumor progression over time during treatment with a nanococktail, the free drugs at the same dose, or the single agents.

For example, during cancer treatment, the addition of the cyclin dependent kinase inhibitor (CDKi) dinaciclib to PARP inhibitor (PARPi) therapy is a strategy to overcome resistance to PARPi in tumors that exhibit homologous recombination (HR) deficiencies as well as to expand PARPi therapy to tumors that do not exhibit HR deficiencies. Combination therapy using pathway inhibitors has been plagued by an inability to administer doses sufficient to achieve clinical benefit due to synergistic toxicities. Combination therapy is of utmost importance for expanding the utility of PARP inhibitors. Dinaciclib, a cyclin dependent kinase inhibitor has been investigated preclinically and clinically as a way to sensitize tumors to PARP inhibition, regardless of HR deficiencies. Clinical use of dinaciclib both as a monotherapy and in combination with PARP inhibitor therapy has been limited by its short plasma half-life and by grade 3-4 toxicity necessitating dose reduction or delay rendering the combination therapy ineffective. The nanoparticulate delivery vehicles herein can provide a nanoformulation of dinaciclib demonstrating similar pharmacodynamics to a nanoformulation of the PARP inhibitor talazoparib. When co-administered in a nanococktail, tumor progression can be slowed in a preclinical breast cancer animal model, while the combination of the free drugs yielded no therapeutic effect (FIG. 9A).

Figure 6A:
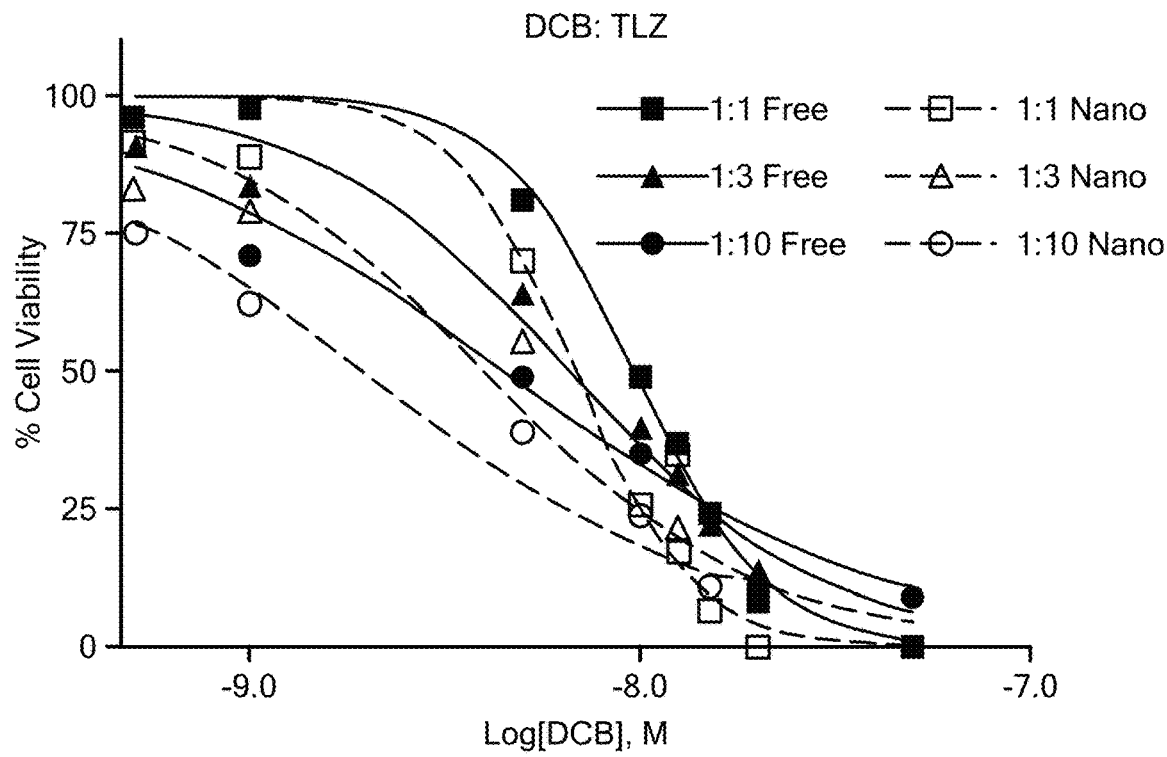
FIG. 6A shows a plot of dose response of TLZ+DCB (free) and nTLZ+nDCB (nanococktail) at three different ratios.
Figure 6B:
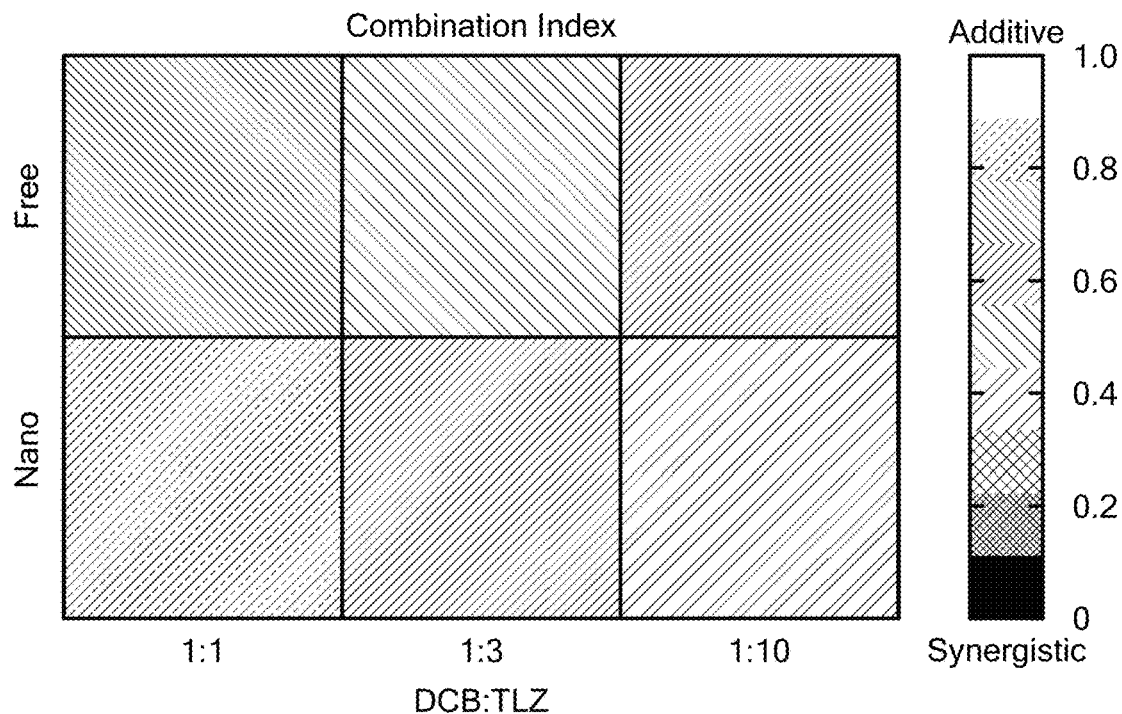
FIG. 6B shows combination indices for the three ratios of TLZ+DCB (free) and nTLZ+nDCB (nanococktail) shown in FIG. 6A.
Figure 6C:
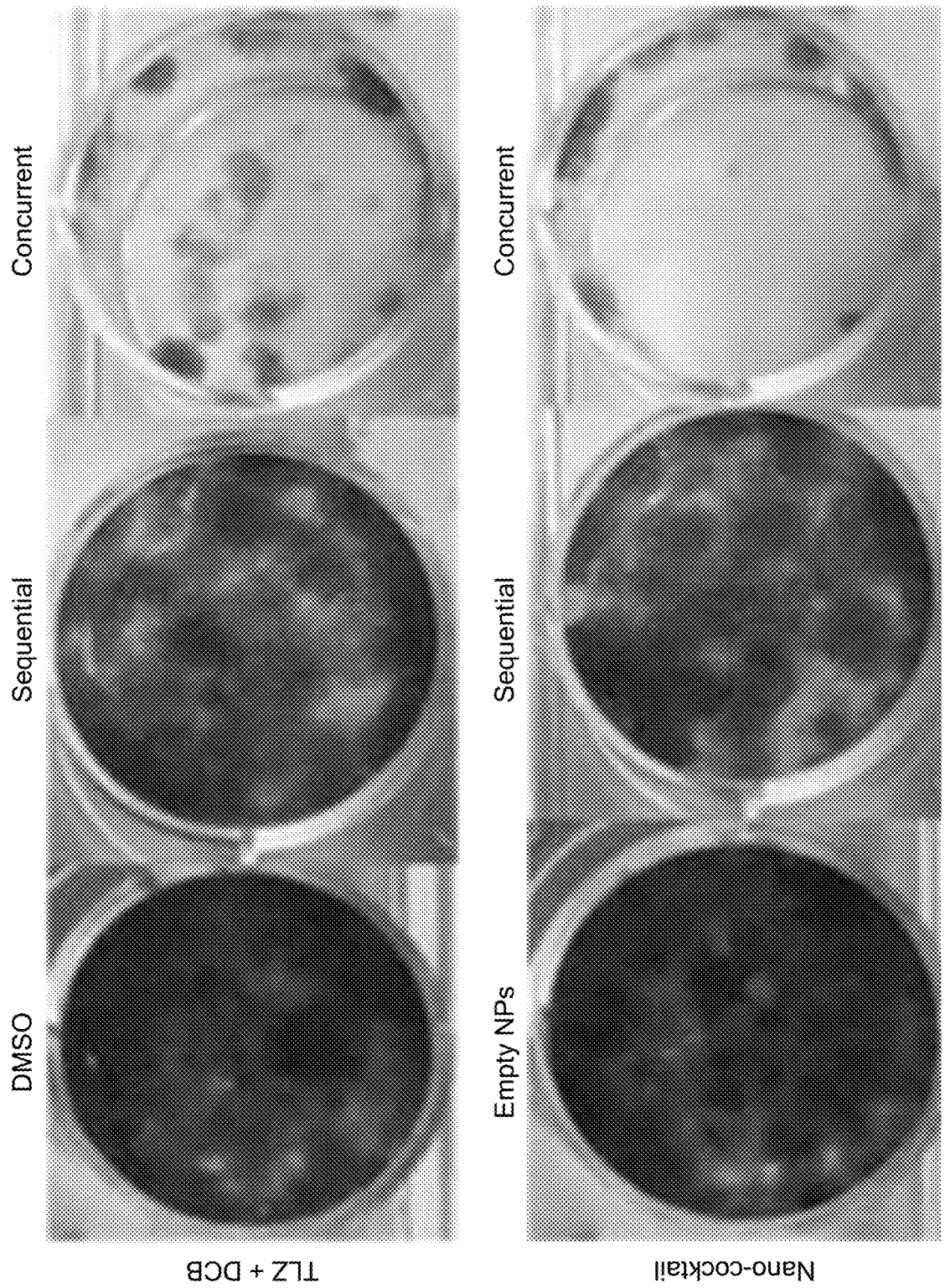
FIG. 6C shows representative images of sequential or concurrent treatment with DCB and TLZ (free) or nDCB and nTLZ (nanococktail). Controls (DMSO or empty nanoparticles) are shown in the images at left.

To design nanoparticulate delivery vehicles including active agents, pharmacokinetics of each nanoparticulate delivery vehicle can be compared, for example, to deliver similar half life (FIG. 7A, FIG. 7B) or to provide maximum overlap between therapeutic windows of active agents. The duration of action of two or more active agents can be maximized. Cell viability for different ratios of the nanoparticulate delivery vehicles can be compared (FIG. 6A, FIG. 6C). The pharmacokinetics of the nanoparticulate delivery vehicles can be compared to that of the free active agents as in Example 2. The pharmacodynamics of the nanoparticulate delivery vehicles can be compared utilizing in vivo studies. A matrix of different variables can be compared to design nanoparticulate delivery vehicles that provide an optimum combination index (FIG. 6B). The optimum combination index can provide larger overlap of therapeutic windows, taking into account adverse effects, synergistic positive effects, and any other variables. Any variables affecting the efficacy of an active agent can be considered, and include, for example, toxicity, pharmacokinetics, adsorption, metabolism, distribution, excretion (ADME), stability, solubility, imaging, and targeting.

Triple-negative breast cancer (TNBC), which lacks expression of the estrogen receptor, progesterone receptor, and human epidermal growth factor receptor 2 amplification, comprises 15-20% of all breast cancers [11]. Although targeted therapies are becoming part of first line treatments for a number of cancers, sequential chemotherapy remains the standard of care for TNBC, due to the lack of receptor expression for targeting [12,13]. Poly-(ADP-ribose) Polymerase (PARP) inhibitors are in clinical trials for treatment of a variety of cancers in which there are defects in the DNA repair pathways, such as BRCA1/2 mutations, which have been observed in 10-20% of TNBC cases in unselected cohorts [14,15]. PARP inhibitors, such as Talazoparib (TLZ), were designed as catalytic inhibitors to block the action of PARP. This hinders repair of DNA single strand breaks converting them to double strand breaks (DSBs) during replication. In cells with mutations in the homologous recombination (HR) pathway this exploits the concept of synthetic lethality, as these cells are unable to repair the generated DSBs with HR [16,17]. Currently, PARP inhibitors are only approved for the treatment of advanced BRCA-mutant breast cancer, meaning at least 80% of TNBC patients are not candidates for this therapy.

Dinaciclib (DCB), a CDK inhibitor, has been shown to potentially ameliorate resistance to PARP inhibition through modulation of DNA repair pathways. Inhibition of CDK1 has been shown to impair the formation of BRCA1 foci at sites of DNA damage, deactivating DNA damage checkpoint signaling [18,19]. Inhibition of either CDK9 or CDK12 has been associated with suppression of DNA damage response and repair genes; in particular, downregulation of RAD51 which results in less RAD51 foci formation at sites of DNA damage [20,21]. DCB has also been shown to decrease expression of MYC, a proto-oncogene amplified in numerous types of cancer [22]. MYC amplification increases the expression of DNA repair genes, notably RAD51, and these patients experience shorter time to relapse and tend to be less sensitive to PARP inhibitor treatment [22,23]. Therefore, DCB can downregulate a number of the key factors in HR in order to sensitize tumors with both intrinsic and acquired PARP inhibitor resistance.

Preclinical studies have demonstrated that the combination of DCB with PARP inhibitors veliparib, olaparib, or niraparib can sensitize resistant models to PARP inhibition and control tumor growth [20-22]. For tumors that are already sensitive to PARP inhibition, this combination has been proven to provide a more durable response than treatment with the PARP inhibitor alone.

In a phase I dose-escalation study of DCB for the treatment of solid tumors 60% of patients in all dose levels experienced grade 3-4 toxicities, with the most common being anemia, hyperbilirubinemia, neutropenia, and hypophosphatemia [24]. In a phase II study investigating DCB to treat advanced breast cancer grade 3-4 adverse events included neutropenia (47%), leukopenia (21%), increased transaminase levels (11%), and febrile neutropenia (11%). Additionally, this study was ended after 30 patients because time to disease progression was shorter for those treated with DCB compared to those treated with capecitabine [25]. Pharmacokinetic assessment revealed the half-life of DCB after a 2 hour infusion is 3.3 hours for a dose of 58 mg/m2 [26]. Additional longer infusions were studied in an effort to prolong the plasma half-life but these schedules resulted in other toxicities which have prevented further development of these schedules.

Preclinical studies did not demonstrate significant toxicity in animals treated with various PARP inhibitors in combination with DCB, leading to the initiation of a clinical trial to assess the combination of DCB and veliparib [20]. The recommended phase 2 dose was 30 mg/m2 DCB every other week and 400 mg veliparib twice daily, however, subsequent cycles required veliparib dose reduction [27]. Preliminary findings suggested patients were more likely to respond when the dose of veliparib was high enough to take advantage of PARP trapping, a phenomenon in which PARP binds to the site of DNA damage and becomes "trapped," generating a cytotoxic lesion [27,28]. Therefore, additional arms were explored in which DCB was administered more often at a lower dose in an effort to maintain the PARP inhibitor dose. The short plasma half-life of DCB may contribute to the difficulty in combining DCB with veliparib.

Of the commercial PARP inhibitors, TLZ is the most potent PARP trapper while veliparib is the least potent [29]. It has been suggested veliparib is the easiest PARP inhibitor to combine with other therapies due to the lack of PARP trapping [30]. Even so, the combination of veliparib and DCB still resulted in dose reduction and suboptimal treatment clinically, suggesting there will be challenges combining DCB with any PARP inhibitor. The present technology provides a nanoformulation of TLZ (nTLZ, Example 1) and demonstrates that the nanoformulation increases both the time to disease progression and overall survival, compared to equivalent doses of i.v. and oral TLZ in a murine model of spontaneous breast cancer [31]. Additionally, treatment with nTLZ does not induce any signs of alopecia, while both oral and i.v. TLZ do elicit this phenotype in 25% of animals. Therefore, nTLZ offers an avenue for combining PARP inhibition with other therapies, such as DCB, with the potential for less toxicity. The short half-life of DCB and incidence of adverse events suggest the combination with nTLZ will not ameliorate all of the challenges associated with DCB combination therapy. The development of a nanoformulation of DCB (nDCB) which can extend the half-life of DCB is better suited for combination with nTLZ. As shown in Examples 3 and 4, the co-delivery of nTLZ and nDCB in a nanococktail results in better efficacy than co-delivery of the free drugs. The overlap of two or more therapeutic windows is increased by the nanoparticulate delivery vehicles. The combination index (FIG. 6B) provides an example of how a matrix of variables can be compared to intelligently design formulations including two or more nanoparticulate delivery vehicles. The nanococktail can reduce the toxicity of the combination by allowing for lower doses to be administered while still providing efficacy.

Figure 7A:
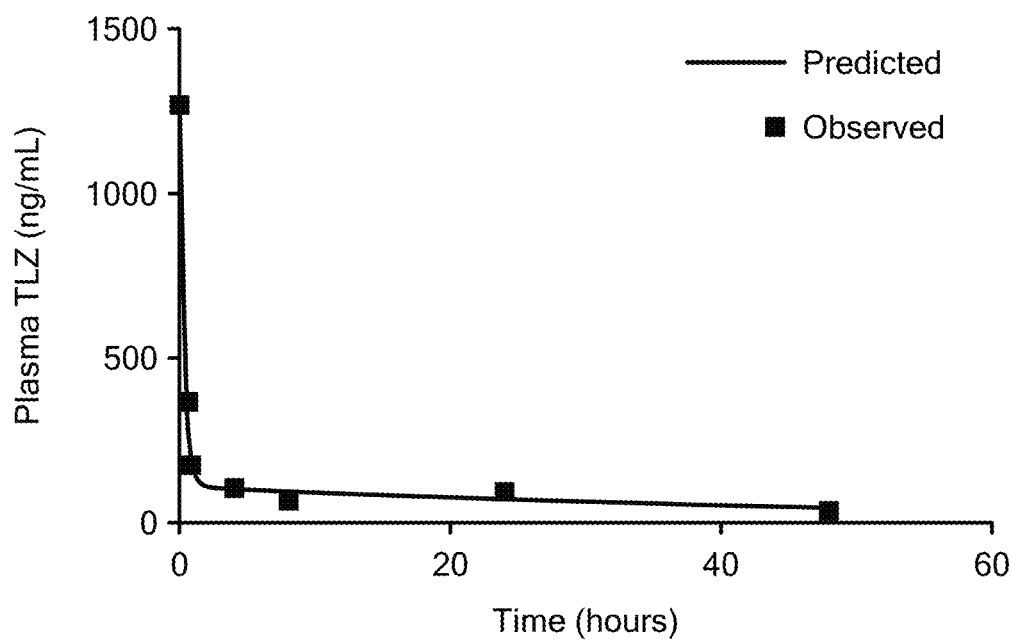
FIG. 7A and FIG. 7B demonstrate the pharmacokinetics of each formulation in the nanococktail.
Figure 7B:
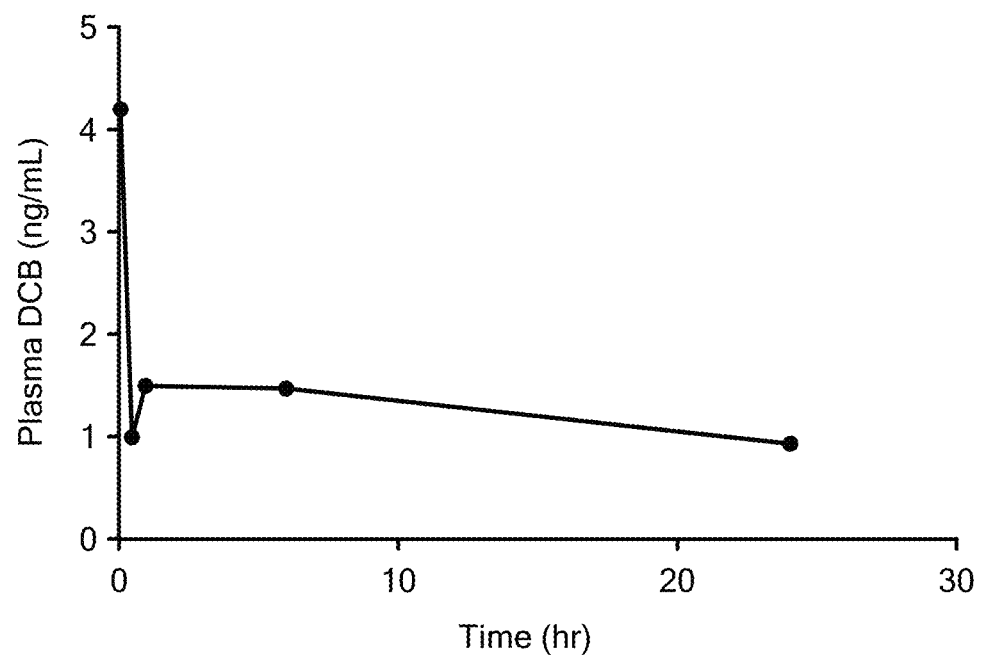

The nanococktails described herein can slow tumor progression and extend survival time, for example, by modifying the pharmacokinetics and pharmacodynamics of the active agents, with or without lowered toxicity, with or without improved solubility, for example. Any of the variables discussed herein can be utilized in the methods with additional variables specific to a treatment or patient. Variables such as plasma drug levels provide examples to demonstrate how the nanoparticulate delivery vehicles are designed and combined. In FIG. 7B, the plasma drug levels of nDCB indicated a half-life of 30.7 hours, in contrast the half-life of free DCB administered intraperitoneally (i.p.) has been reported to be 0.25 hours, suggesting the nanoparticle (nanoparticulate delivery vehicle) drastically altered the pharmacokinetics of the compound [38]. It is important to note differences in the experimental design in that the reported half-life of free DCB was after an i.p. administration of 5 mg/kg DCB and Example 3 demonstrates a 1 mg/kg i.v. injection of nDCB, meaning these half-lives are not directly comparable. The RAD51 expression in the tumors explained in Example 3 shows nDCB accumulates at the tumor and disrupts the HR pathway for up to 24 hours.

RAD51 expression has been proposed as a biomarker for stratifying PARP inhibitor response, suggesting that tumors should be sensitive to PARP inhibition for at least 24 hours after nDCB treatment [22,38]. nTLZ elicits 90% inhibition of PARP in the tumor for up to 8 hours and 50% inhibition up to 72 hours after administration [31]. The overlapping pharmacodynamic profiles indicate nDCB and nTLZ should work in concert with one another if administered as a nanococktail, and it is expected this was the reason therapeutic benefit is observed with nTLZ+nDCB and not with free TLZ+free DCB.

Figure 10A:
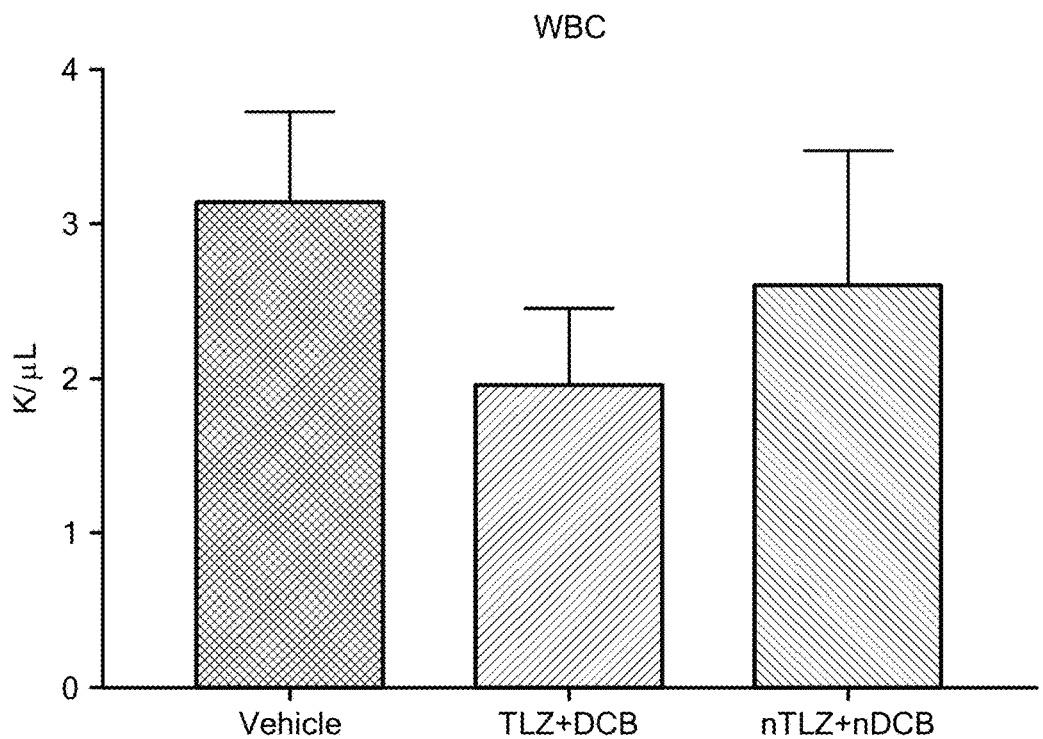
FIG. 10A shows hematologic toxicity of TLZ+DCB and nTLZ+nDCB assessed by WBC.
Figure 10B:
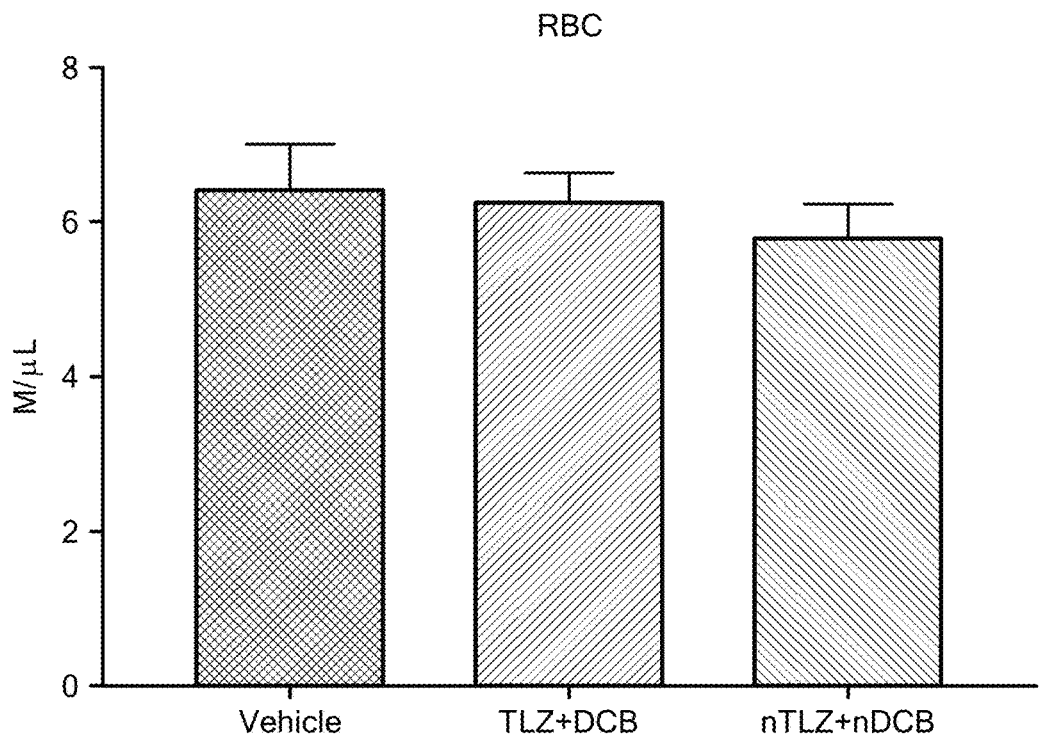
FIG. 10B shows hematologic toxicity of TLZ+DCB and nTLZ+nDCB assessed by RBC.
Figure 10C:
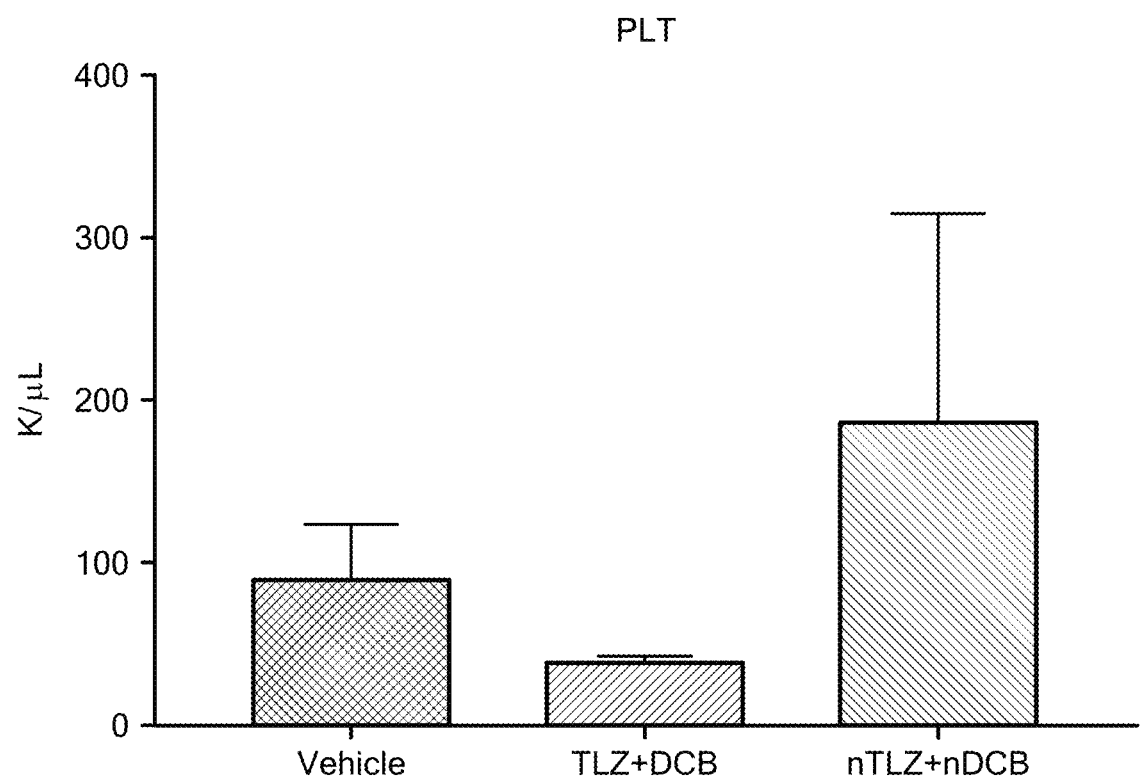
FIG. 10C shows hematologic toxicity of TLZ+DCB and nTLZ+nDCB assessed by PLT count.
Figure 10D:
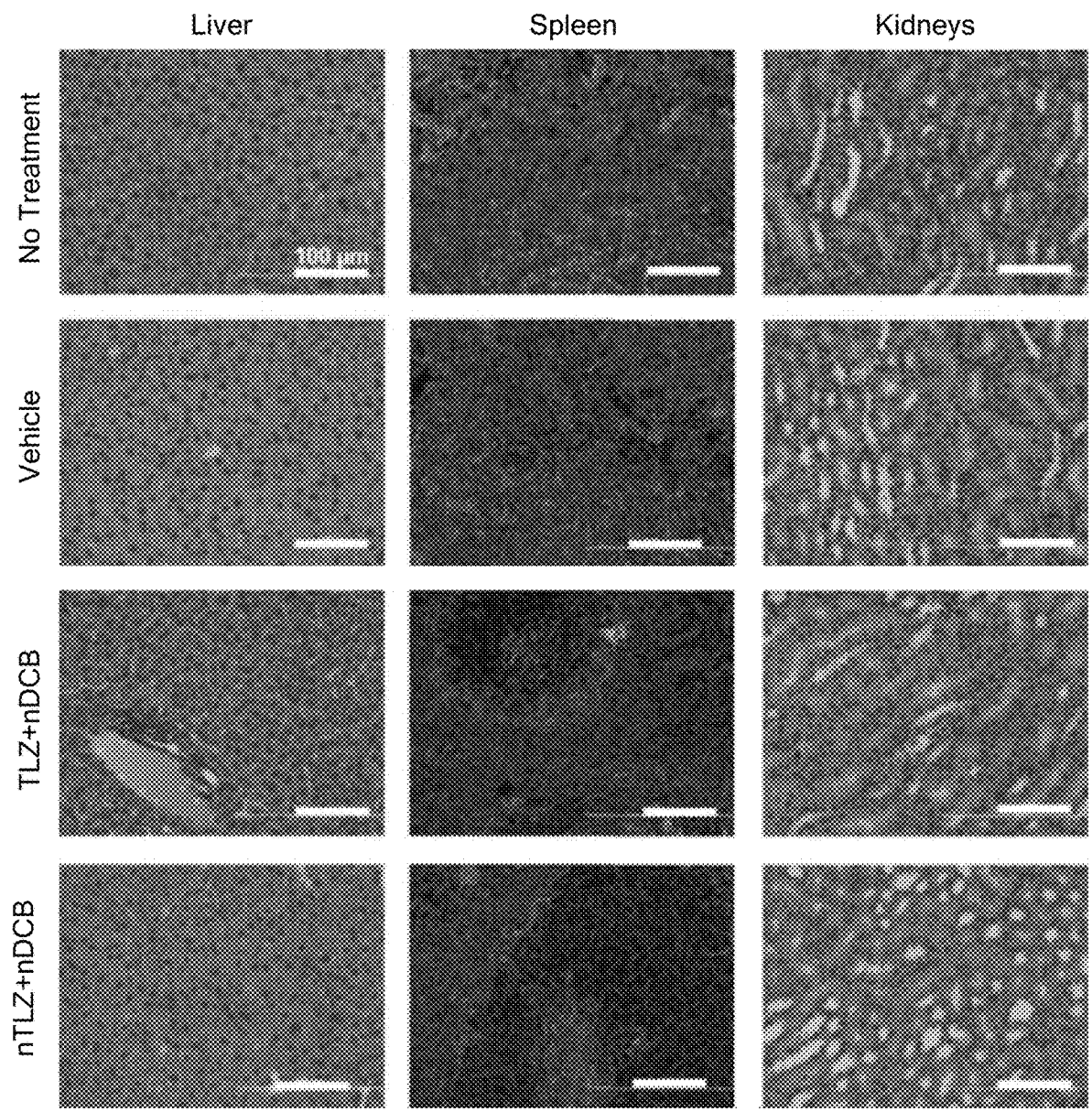
FIG. 10D shows images of slices of kidneys, livers, and spleens stained with hematoxylin and eosin (H&E) stain for the various treatments, demonstrating no gross morphological organ damage. The scale bar is 100 µm.

Johnson et al. demonstrated the utility of DCB with the PARP inhibitors olaparib and veliparib in models that were both PARP inhibitor sensitive and resistant [20]. 154 days of treatment at 30 mg/kg DCB 2× weekly and 50 mg/kg veliparib 2× daily was not found to induce end-organ toxicity, suggesting the combination is tolerable. However, as the combination of veliparib and DCB progressed into a phase I clinical trial tolerable doses were achieved, but overall patient responses were modest, and additional tolerable dosing regimens were to be pursued [27]. In a phase III clinical trial 52% of patients treated with oral TLZ presented with anemia, low RBC count, 27% thrombocytopenia, low PLT count, and 17% leukopenia, low WBC count [39]. Only 3% of patients treated with DCB presented with thrombocytopenia [26]. Neutropenia, a depletion of a subset of WBCs, is common between both drugs, with 35% of patients treated with TLZ and 43% treated with DCB experiencing this condition. After 3 doses of DCB and TLZ or nTLZ+nDCB, no significant differences in any of the blood cell counts were observed with either combination compared to vehicle, though the WBC and PLT counts for the free combination were slightly lower (FIGS. 10A-10C). This data demonstrates that at the doses utilized in the Examples, these side effects have not yet manifested. Additionally, the histology indicated no nanoparticle or drug induced morphological changes to the kidneys, liver, or spleens (FIG. 10D).

The therapeutic benefit offered by nTLZ+nDCB compared to the combination of free TLZ and free DCB combined with a lack of observed toxicity provides a rationale for dose-escalation. This study presents proof-of-concept that a nanococktail composed of two formulations with similar pharmacodynamics (PD) profiles can be used to rationally administer combination therapies. The efficacy data combined with a lack of observed hematologic toxicity or organ related toxicity suggests dose-escalation is a viable next step to achieve disease stabilization or regression.

The outbreak of Coronavirus Disease 2019 (COVID-19) has posed a serious threat to global public health, calling for the development of safe and effective prophylactics and therapeutics against infection of its causative agent, severe acute respiratory syndrome coronavirus 2 (SARS-CoV-2), also known as 2019 novel coronavirus (2019-nCoV). The CoV spike (S) protein plays the most significant roles in viral attachment, fusion and entry to human cells through angiotensin-converting enzyme 2 (ACE2) receptors. Recently, researchers have identified the receptor-binding domain (RBD) in SARS-CoV-2 S protein and confirmed that the RBD protein has strong binding affinity to human ACE2 receptors (Tai et al. 2020). Thus, SARS-CoV-2 S protein can serve as a target for the development potential inhibitors that block the interaction between SARS-CoV-2 RBD and ACE2-expressing cells, thus inhibiting the infection of 2019-nCoV to host cells.

During the 2003 outbreak of SARS, passive immunization using convalescent plasma with high titers of neutralizing antibody was used for the treatment of SARS-CoV patients (Cheng et al. 2005) (Yeh et al. 2005). Currently, hyperimmune globulin produced from plasma from convalescent patients and equine plasma produced by immunization with inactivated SARS-CoV are available for prophylactic trials in humans (Lu et al. 2005) (Zhang et al. 2005). Interestingly, SARS-CoV RBD-specific antibodies could cross-react with SARS-CoV-2 RBD protein, and SARS-CoV RBD-induced antisera could cross-neutralize SARS-CoV-2 (Tian et al. 2020), suggesting the potential to develop SARS-CoV RBD-based vaccines for prevention of SARS-CoV as well as SARS-CoV-2 infections.

Current studies have revealed that cell entry of SARS-CoV-2 is facilitated by binding of S protein to ACE2 receptors followed by S protein priming by host cell proteases. It is now elucidated that SARS-CoV can use cysteine proteases cathepsin B and L (CatB/L) (Simmons et al. 2005) and transmembrane protease serine 2 (TMPRSS2) (Shulla et al. 2011) (Matsuyama et al. 2010) for S protein priming for their entry to the host cells. Hence, inhibition of these proteases led to robust blockade of viral entry (Kawase et al. 2012). However, several reports have confirmed that TMPRSS2 activity is determinant for viral spread and pathogenesis while CatB/L activity is dispensable (Iwata-Yoshikawa et al. 2019) (Shirato, Kawase, and Matsuyama 2018). Of note, an inhibition of TMPRSS2 activity might constitute a treatment option to block the entry of the viruses and hence infections. In fact, a TMPRSS2 inhibitor, Camostat mesylate, partially blocked SARS-2-S-driven entry into Caco-2 and Vero-TMPRSS2 cells (Hoffmann et al. 2020) indicating the potential use of the inhibitor against SARS-CoV-2 infection.

Figure 11A:
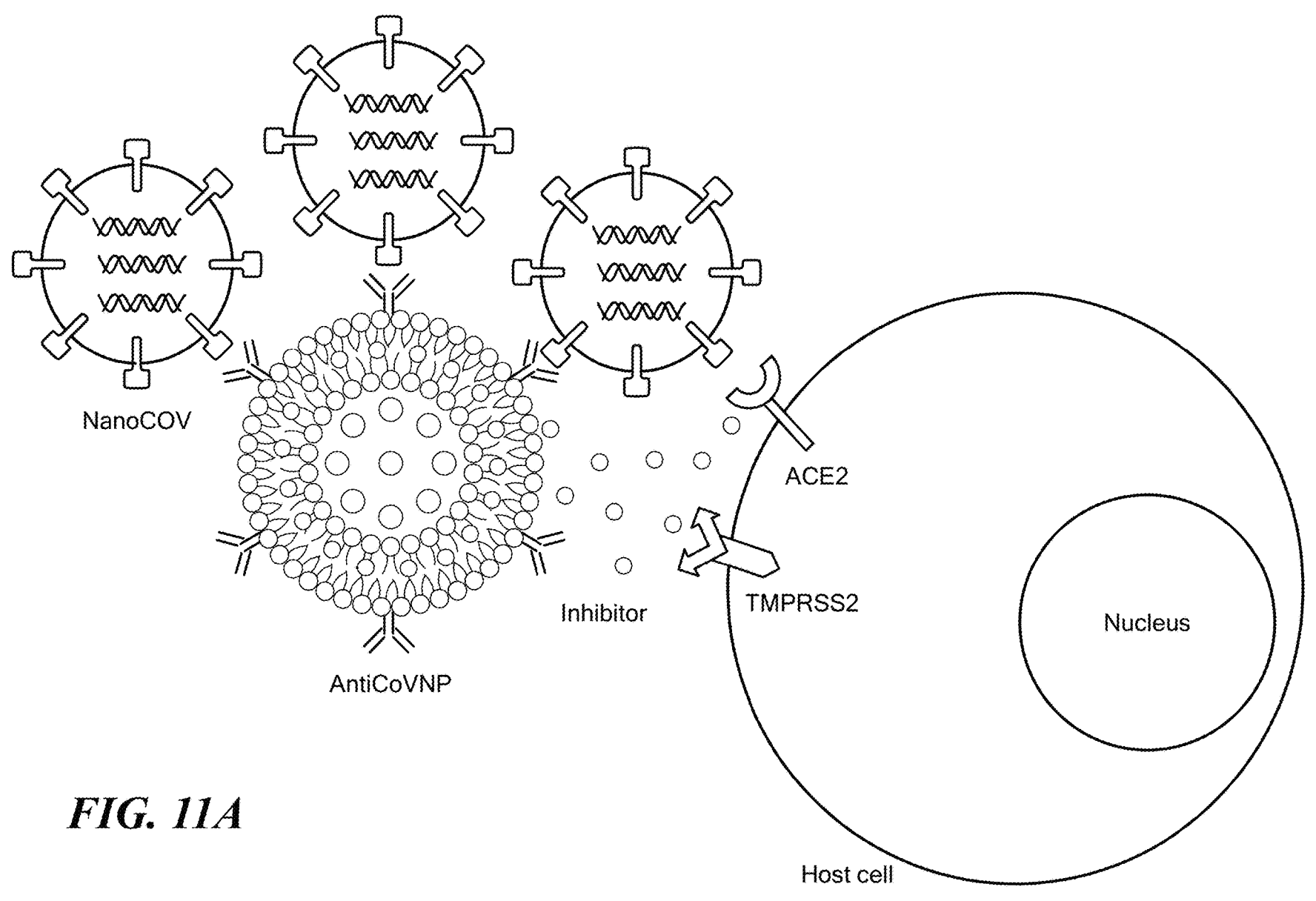

The synthesis of a virus mimicking "AntiCoVNP" can be specifically tailored according to the physicochemical properties of the drugs or antibodies involved. Anti-COVID Nanoparticles (AntiCoVNPs) can be designed utilizing the present technology. The nanotherapeutic AntiCoVNPs are lipid nanoparticles that can be synthesized using a fixed ratio of pegylated lipids. Any of the therapeutic agents listed in Table 2 can be administered utilizing a separate nanoparticulate delivery vehicle or can be incorporated into the AntiCoVNPs. To impart functionality on the surface of the nanoparticles, SARS-CoV RBD-specific antibodies can be decorated. AntiCoVNPs thus developed can be used to prevent the viral infections by dual mechanisms. First, they neutralize the multiple SARS-CoV-2 S proteins of the viruses and second, they inhibit the entry of the virus into host cells by the released protease inhibitor drugs. Nano-COV is a virus mimicking lipid corona type nanoparticle with Spike protein on the surface. This is necessary to perform in vitro tests without the live virus. An illustration of blocking of virus mimicking particles (NanoCOV) into cells by AntiCoVNP using antibody and drug inhibitors is shown in FIG. 11A.

Figure 11B:
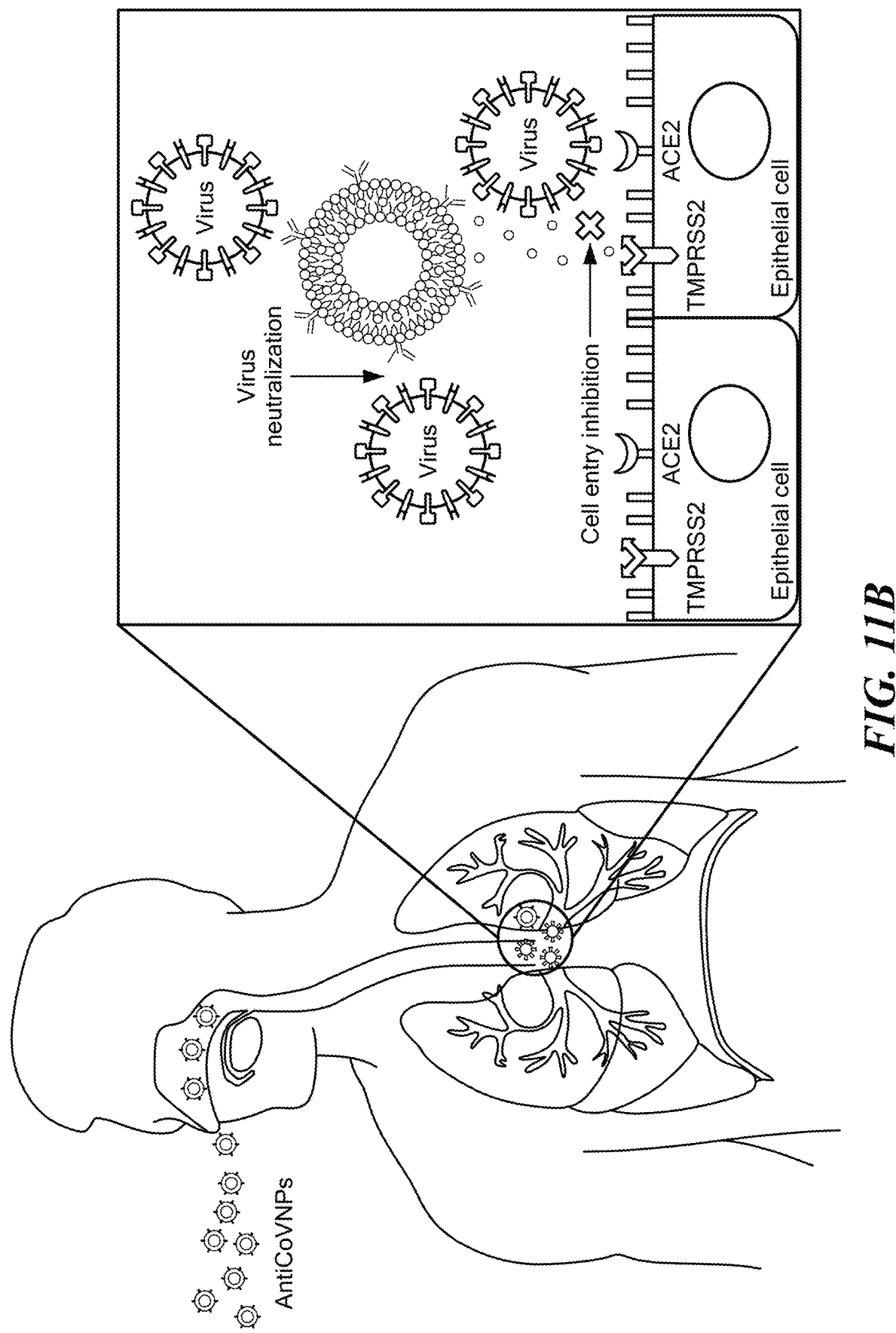
FIG. 11B illustrates aerosol delivery of AntiCoVNPs to combat viruses either by antibody-mediated neutralization or drug-mediated inhibition of cell entry or replication of virus.

In the clinic, AntiCoVNPs can be administered via pulmonary inhalation leading to direct deposit of AntiCoVNPs in the airway tract of the lungs, or parenteral injection for other organs infected by the viruses. AntiCoVNPs can block the infection of viruses by neutralizing the viruses and providing co-inhibition of viral entry to cells either of which results in significantly more effective viral destruction. FIG. 11B presents an illustration of aerosol delivery of Anti-CoVNPs to combat viruses either by antibody-mediated neutralization or drug-mediated inhibition of cell entry of virus.

One nanoparticulate delivery vehicle may include an active agent for a particular class of activity, for example, an antiviral. Another nanoparticulate delivery vehicle can include an active agent for a different class of activity. Examples of antivirals are lopinavir/ritonavir, favipiravir, remdesivir, umifenovir, oseltamivir, darunavir, atazanavir/ritonavir, clevudine, and merimepodib. Another nanoparticulate delivery vehicle can include an active agent for antibiotic, antiproliferative, immunomodulatory, immunosuppressant, or immunostimulant activity, for example. Examples of immunosuppressants are tocilizumab, sarilumab, colchicine, anakinra, dexamethasone, cyclosporine, siltuximab, adalimumab, and ruxolitinib. Examples of antibiotics are azithromycin and carrimycin. For example, by utilizing two or more nanoparticulate delivery vehicles to deliver an immunomodulatory (e.g., imatinib) on one nanoparticulate delivery vehicle and to delivery an antiviral on another nanoparticulate delivery vehicle, the overlap between therapeutic windows (or targeted effects) of two or more classes of active agents can be combined and tuned for pharmacokinetics, pharmacodynamics, targeting, solubility, duration of action, and maximum benefit for a patient.

For treatment of COVID-19 with overlapping therapeutic windows of two or more active agents, one nanoparticulate delivery vehicle can be utilized with one class of active agent that has a known free therapeutic window, include adverse and beneficial effects over time. The therapeutic window can be measured by variables including solubility, pharmacodynamics, pharmacokinetics, duration of action, and toxicity, for example. A second nanoparticulate delivery vehicle can be utilized with a second class of active agent that has a second known, free therapeutic window. By utilizing a method of making a pharmaceutical formulation herein, the first nanoparticulate delivery vehicle can be planned to provide a different therapeutic window compared to the first active agent without the nanoparticulate delivery vehicle. At first, initial assessment of the free active agents (and the nanoparticulate delivery vehicles including active agents) can include, for example, physicochemical characterization (Example 5). Later, the serum half-life (FIG. 7A, FIG. 7B), and cell viability (FIG. 6A) can be considered. As nanoparticulate delivery vehicles are synthesized, assessments can broaden to more expensive in vivo experiments (e.g., FIG. 8A, 8B, 9A, Examples 3 and 4). Accordingly, the methods of making pharmaceutical compositions provided herein can be intelligent, gradient approach methods. Gradient approach methods, as described herein are wherein an initial comparison of a free active agent and a nanoparticulate delivery vehicle including an active agent provides sufficient information to determine if the nanoparticulate delivery vehicle should be resynthesized, treated, or re-treated (to change, for example, size or charge) or if it can proceed to a combination therapy with more extensive (or expensive) testing. The initial comparisons can be lower cost, for example, measurement of particle size, zeta potential, polydispersity index, and release profile. As greater confidence and knowledge in the physicochemical characterizations is gained for specific nanoparticulate delivery vehicles including active agents, experiments such as serum half-life, cell viability, or pharmacodynamics can be considered. Importantly, the intelligent, gradient approach methods allow combination of any ratio of one nanoparticulate delivery vehicle including one active agent with one or more other nanoparticulate delivery vehicles, each including (one or more) active agent. Each step of formulation design can be done by gradient approach. Characterization of a single nanoparticulate delivery vehicle with active agent compared to free active agent, optimization of the nanoparticulate delivery vehicles with the active agent, can be done before forming a formulation including two or more nanoparticulate delivery vehicles.

The second nanoparticulate delivery vehicle can be designed to provide a different therapeutic window compared to the second free active agent without the nanoparticulate delivery vehicle. The overlap between the therapeutic windows of the first active agent and the second active agent, with the nanoparticulate delivery vehicles, can be designed to minimize toxicity, to maximize overlapping durations of action, to maximize overlapping serum half lives, to provide maximum pharmacodynamics, to maximize solubility, and to prevent degradation, for example. The overlap can be determined by a health care professional just before administration to a patient, taking into account the patient's immediate condition, lab results, temperature, susceptibility, resistance, or conditions. The comparison can be provided for one or more dimensions (variables) in a combination index (FIG. 6B). The route of administration of the nanoparticulate delivery vehicles can be by any route known in the art, and the route of administration is taken into account when designing the nanoparticulate delivery vehicles.

TABLE 2

| Examples of COVID-19 Therapies | | |
|---|---|---|
| Alternative therapy | Inhaled solution | Antiplatelets |
| Plasma based therapy | Oseltamivir | antivirals |
| Traditional Chinese Medicine | Cyclosporine | Atazanavir/ritonavir |
| Lopinavir/ritonavir | Melatonin | Azithromycin or Lopinavir/ritonavir |
| Vaccine | Cytokine removal | AZT |
| Azithromycin | Imatinib | Chloroquines |
| Stem cell therapy | ACEi | Clevudine |
| mAb | Anesthetic | Cotrimoxazole |
| Tocilizumab | Natural Killer Cells | Cyclosporin |
| Interferon | Acalabrutinib | DHODH inhibitor |
| Vitamins | ECMO | Docycline |
| Corticosteroids | mAB | DRV/c |
| Anticoagulants | Siltuximab | DRV/r |
| Favipiravir | Antiretroviral | Estrogen steroid hormone |
| JAKi | SGLT2 | Hemoperfusion |
| Ivermectin | DMARD | Lithium +/− Azithromycin |
| Antivirals | DPP-4i | Lopinavir/ritonavir (or |
| Immunoglobulins | Antiretrovirals | Lopinavir/ritonavir or Atazanavir |

TABLE 2-continued Examples of COVID-19 Therapies

| | | |
|---|---|---|
| Remdesivir | Antithrombotics | Lopinavir/ritonavir or AZT |
| ARBs | Bisphosphonate | losartan |
| DAA | Carrimycin | Merimepodib |
| Immunomodulators | CCB | Opiate analgesics |
| Sarilumab | Chemotherapy | Opiate antagonists |
| Zinc | Darunavir | Pirfenidone |
| Colchicine | DPP1 inhibitor | Raltagravir |
| Umifenovir | Hydroxychloroquine | RAS blockade |
| Anakinra | Lithium | Respiratory stimulant |
| Antibiotics | NRTIs | Rintatolimod |
| Device | Polyphenols | Ruxolitinib |
| Antihypertensive | SSRIs | SPC |
| Radiation therapy | (hydroxy)chloroquine +/− Azithromycin | Steroids |
| Vasodilators | (hydroxy)chloroquine or Lopinavir/ritonavir or Umifenovir | Sulfate |
| Dexamethasone | Adalimumab | Thrombolytics |
| Hormone therapy | Amoxicillin/clavulanate | TNF inhibitor |
| NSAIDs | Anakinra with/without JAKi antibiotics | |
| Statins | Tocilizumab or Anakinra | |

The present technology can provide a pharmaceutical formulation comprising a suspension, paste, or solid comprising a first nanoparticulate delivery vehicle comprising a first active agent and a second nanoparticulate delivery vehicle comprising a second active agent. The suspension, paste, or solid can be diluted or formulated by a health care provider and subjected to one or more additional steps (e.g., sterile filtration, irradiation, sonication). Additional nanoparticulate delivery vehicles can be added, each including an additional one or more active agents. The nanoparticulate delivery vehicles can be, for example, any nanoparticle known in the art such as polymeric nanoparticles, metallic nanoparticles, liposomes, micelles, and solid lipid nanoparticles. The average particle size of the first and second nanoparticulate delivery vehicles (and additional nanoparticulate delivery vehicles if added) can be less than 500 nm, less than 400 nm, less than 300 nm, less than 200 nm, less than 100 nm, or less than 50 nm after the first and second nanoparticulate delivery vehicles are combined for a time at a temperature. The polydispersity index of the first and second nanoparticulate delivery vehicles (and additional nanoparticulate delivery vehicles) can change from time zero up to a time, by less than about 0.25, by less than about 0.20, by less than about 0.15, by less than about 0.10, or by less than about 0.05 after the first and second nanoparticulate delivery vehicles are combined for a time at a temperature. The time can be 24 hours, 1 week, 2 weeks, 3 weeks, 1 month, 5 weeks, 6 weeks, 7 week, or 8 weeks after the combining. The time can be measured after administration to a subject. The temperature can be in the range from about 0° C. to about 40° C., about 4° C. to about 30° C., about 4° C. to about 25° C., about 4° C. to about 20° C., about 4° C. to about 10° C., and about 4° C. to about 8° C. The nanoparticulate delivery vehicles essentially do not aggregate to form larger, aggregated particles.

The difference between the zeta potentials of any of the nanoparticulate (e.g., first, second, third) delivery vehicles is in the range from about 0 mV to about 40 mV. The difference between the zeta potentials of any of the nanoparticulate delivery vehicles is not more than about 15 mV, is not more than about 20 mV, is not more than about 25 mV, or is not more than about 30 mV. The zeta potentials of the nanoparticulate delivery vehicles can each have a zeta potential in the range from about +5 mV to +60 mV, from about +15 mV to +60 mV, from about +15 mV to +50 mV, from about +15 mV to +40 mV, or from about +15 mV to +30 mV. The zeta potentials of the nanoparticulate delivery vehicles can each have a zeta potential in the range from about −5 mV to −60 mV, from about −15 mV to −60 mV, from about −5 mV to −50 mV, from about −5 mV to −40 mV, or from about −5 mV to −30 mV. If the nanoparticulate delivery vehicles are near neutral, the nanoparticulate delivery vehicles can each have a zeta potential in the range from about −20 mV to +20 mV, from about −15 mV to +15 mV, from about −10 mV to +10 mV, or from about −5 mV to +5 mV. The zeta potentials of the nanoparticulate delivery vehicles can be designed during synthesis by, for example, adding charged molecules, ions, active agents, peptides, oligonucleotides, oligopeptides, poly-beta-amino-esters, surfactants, buffers, or a combination thereof. The zeta potentials of the nanoparticulate delivery vehicles can be changed after synthesis, for example, by pressure with an agent, by sonic mixing, by homogenization with a charged solute, by exposure to ionizing energy, by exposure to a partial or full coating, by filling of pores, by removal of protrusions or spikes.

The active agents to be utilized in the compositions and methods of the present technology are not limited. For example, any two or more active agents can be compared in the free form, without the nanoparticulate delivery vehicles. By comparing free therapeutic windows, duration of action, toxicity, for example, in the free form, a desired (targeted) overlap between therapeutic windows can be planned. Next, two or more nanoparticulate delivery vehicles are designed, while taking into account charge on the two or more active agents and planned route of administration. The zeta potentials of the two or more nanoparticulate delivery vehicles are designed. Solubility of the two or more active agents is planned along with serum half life, degradation, and duration of action. The two or more nanoparticulate delivery vehicles are synthesized and can be tested in vitro, with the results compared to corresponding results for the free active agents, without the nanoparticulate delivery vehicles. A greater overlap between the therapeutic windows for the active agents can be achieved with the nanoparticulate delivery vehicles. After synthesis, the amount of any nanoparticulate delivery vehicle in the pharmaceutical formulation can be changed without changing the amount of any other nanoparticulate delivery vehicle.

For example, specific patient conditions can be taken into consideration. If a patient is immunocompromised, less of a nanoparticulate delivery vehicle can be added to the formulation for that individual patient than would be added for a patient who is not immunocompromised, or a nanoparticulate delivery vehicle can be utilized with a slower release profile to minimize acute toxicity for the specific patient. If a patient has a liver condition, the toxicity and clearance of a pharmaceutical formulation can be adjusted specific to that individual patient. The technology can provide a kit including containers of individual nanoparticulate delivery vehicles, each including a different active agent. The release profile or duration of each active agent on each nanoparticulate delivery vehicle can be provided. Instructions can be provided to describe how much of one nanoparticulate delivery vehicle to combine with another for specific patients with specific lab results. Specific lab result ranges can be provided with the instructions, for example, the instructions can include ranges for transaminases, aspartate transaminase, and alanine transaminase and corresponding ranges for mixing nanoparticulate delivery vehicles into formulations for specific patients falling within the set liver conditions. If a patient is under the effects of alcohol or other drugs, these factors can be taken into account in making the pharmaceutical formulation for that patient. In another example, the nanoparticulate delivery vehicles are provided unmixed in an inhaler with a dial setting that can change the proportion of nanoparticulate delivery vehicles mixed together by changing the setting on the dial. The dial can move a valve inside the inhaler to mix different proportions of the nanoparticulate delivery vehicles. The nanoparticulate delivery vehicles can be provided in an injector that can be preset before injection to provide a specific proportion of a first nanoparticulate delivery vehicle, a second nanoparticulate delivery vehicle, and additional nanoparticulate delivery vehicles as needed for more complex treatments.

For treatment of COVID-19 by via pulmonary inhalation, different proportions of nanoparticulate delivery vehicles can be provided to a patient with compromised immune system, a patient with lung cancer, a patient with pneumonia, a patient on a ventilator, a patient with a fever, for example.

The medical conditions and diseases that can be treated or prevented with the technology provided herein are not limited. For example, traumatic injuries such as brain injury, concussions, wounds, or surgery can be treated by combinations of the nanoparticulate delivery vehicles described herein. Any medical condition, disease, or injury that can respond to two or more active agents can be considered.

EXAMPLES

Example 1: Synthesis of Formulations for Nanococktail

For synthesis of nDCB, poly(D,L-lactide-co-glycolide), PLGA and mPEG-PLGA were utilized to create a polymeric nanoparticle in which DCB was embedded within the PLGA core. 50:50, acid terminated, $M_w$ 7,000-17,000 (PLGA) and Methoxy Poly(ethylene glycol)-b-Poly(lactic-co-glycolic acid), 50:50, $M_w$~5000:10000 (mPEG-PLGA) from Sigma Aldrich and PolySciTech, respectively were both dissolved in acetonitrile. The weight ratio of the two components was varied systematically from 10:0 mPEG-PLGA:PLGA to 1:9. Dinaciclib was purchased from MedChem Express and dissolved in DMSO prior to addition to the polymer mixture (10 wt %). Nanoparticles were formed via nanoprecipitation using the NanoAssemblr Benchtop with deionized (DI) water as the aqueous phase using a 2:8 ratio of PLGA:mPEG-PLGA at a total polymer concentration of 50 mg/mL. The aqueous to organic flow rate ratio was 4:1 and the total flow rate was 8 mL/minute. The organic solvent and free drug molecules were removed by washing the formulation twice at 2100 rcf for 15 minutes using a Macrosep Advance Centrifugal Device with a molecular weight cutoff of 100K. After washing the formulation was resuspended using 10×PBS and DI water to a final concentration of 1×PBS. Vehicle nanoparticles were synthesized in the same manner without the addition of dinaciclib. FIG. 3A shows particle size measured by DLS. FIG. 3B presents a transmission electron micrograph of the nanoparticles. The scale bar represents 100 nm.

The stability of nDCB in storage was measured for up to two months after synthesis. All formulations were stored at 4° C. Size, polydispersity, and zeta potential were measured 1 week, 2 weeks, 1 month, and two months post synthesis as described above (FIG. 3D, FIG. 3E). All studies were conducted in triplicate. Size, polydispersity, and zeta potential measurements over time revealed the formulation remained stable in physicochemical properties over the course of 2 months in storage at 4° C.

150 μL of nDCB was added to individual Thermo Scientific Slide-A-Lyzer MINI dialysis unit (10K MWCO) and placed in a PBS bath, pH 7.4 at 37° C., under constant stirring, to produce sink conditions. At predetermined time points (0.5, 1, 2, 4, 6, 8, 10, 24, 30 hrs), an aliquot of the nanoparticle solution was removed and lysed for HPLC analysis. All studies were conducted in triplicate. DLS revealed the hydrodynamic diameter of nDCB to be 46.1±3.8 nm, while TEM confirmed this size distribution (FIG. 3B). nDCB was found to release fully over the course of 30 hours, with ~80% of the drug releasing within the first 8-10 hours (FIG. 3C).

For synthesis of nTLZ, 1, 2-dipalmitoyl-sn-glycero-3-phosphocholine (DPPC), 1,2-dioleoyl-3-tri methyl-ammonium-propane (chloride salt) (DOTAP), cholesterol, and 1,2-distearoyl-sn-glycero-3 phosphoethanolamine-N-[methoxy(polyethyleneglycol)-2000 (DSPE-PEG2000) purchased from Avanti Polar Lipids and talazoparib purchased from Selleck Chemicals were individually dissolved in a methanol/ethanol mixture at a molar ratio of 65:29:2:4. The final mixture contained 2.16 mM talazoparib in dimethylformamide. The aqueous phase for formulation was PBS pH 7.4. Nanoparticles were formed via nanoprecipitation using the NanoAssemblr Benchtop. Organic solvents were removed by evaporation under argon followed by dialysis against PBS for 30 minutes. The non-encapsulated drug, which is insoluble in aqueous media, was removed via syringe filter. Vehicle nanoparticles (empty nanoparticles) were prepared following the same protocol without the addition of talazoparib. FIG. 4B presents a transmission electron micrograph of the nanoparticles. The scale bar represents 500 nm. FIG. 5A presents DLS size distribution of the nTLZ.

Example 2: nDCB Synergizes with nTLZ In Vitro

MDA-MB-231-LUC-D3H2LN (231) cells were provided by Zdravka Medarova (Massachusetts General Hospital, Boston, Mass.) and cultured in DMEM with 10% FBS and 1% Pen/Strep (Corning Cellgro). All studies were conducted in triplicate. 231 cells were seeded into 96 well plates at 1,000 cells per well. The following day, cells were exposed to either DCB or nDCB at concentrations ranging from 0-50 nM or TLZ or nTLZ doses ranging from 0-10 μM. For fixed ratios of DCB:TLZ the DCB and nDCB concentrations ranged from 0-50 nM. Therefore, the TLZ and nTLZ concentrations ranged from 0-50 nM, 0-150 nM, or 0-500 nM for 1:1, 1:3, and 1:10, respectively. One week after seeding, cell viability was ascertained by the MTS assay to measure the metabolic activity of the cells. Data from dose response experiment were plotted and fit using a variable slope four-parameter logistic equation constrained at 100 and 0. Combination indices were calculated using Compusyn [34].

Long-term viability at a ratio of 1:10 DCB:TLZ was assessed using two different dosing regimens. 1,000 cells were seeded into 12 well plates. The following day, cells were treated with doses of 10 nM TLZ and 1 nM DCB. Equivalent dosing was used for nTLZ and nDCB treatment. After 6 days of treatment, the media was replaced, and cells were allowed to grow drug-free for an additional 7 days. In an alternative scheme, cells were treated sequentially with either 1 nM DCB or nDCB for 3 days, followed by a 3 day treatment with either 10 nM TLZ or nTLZ. After the treatment period, the media was replaced, and cells grew drug-free for 7 days. Cells were then fixed with formalin and stained with crystal violet. To quantify the cell growth, the crystal violet was solubilized with 5% acetic acid under gentle shaking, and the absorbance was measured at 563 nm.

To assess protein expression cells were seeded at a density of 20,000/cm$^2$. The following day, cells were treated with either 250 nM TLZ or nTLZ, 25 nM DCB or nDCB, or the respective combinations. After 48 hours of treatment, cells were harvested and lysed for western blotting. Total protein content was determined using the BCA assay. 20 μg of protein were separated on 4-20% polyacrylamide gels and transferred to PDVF membranes. Primary antibodies included γ-H2AX (Cell signaling, 1:1000) and β-ACTIN (Cell signaling, 1:1000). The secondary antibody was HRP-linked anti-rabbit (Cell signaling, 1:2000) and ECL substrate was used for detection.

As shown in FIG. 6A, as the TLZ concentration increased from 1:1 to 1:3 to 1:10 cell viability decreased. At all ratios the viability of cells treated with nTLZ+nDCB was lower than that of cells treated with the equivalent doses of free DCB and TLZ (FIG. 6A, FIG. 6C). The combination indices (CI) indicated all ratios were synergistic, with 1:1 for both free drugs and nanoformulations exhibiting the least synergism (FIG. 6B).

Figure 6D:
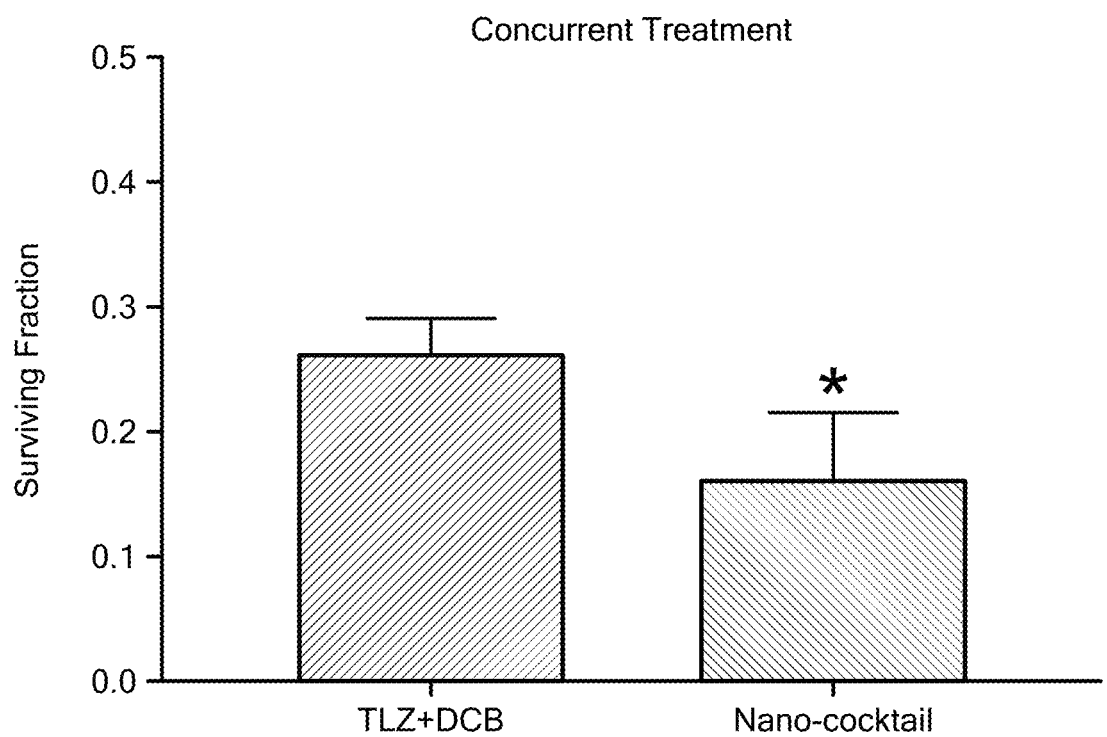
FIG. 6D shows quantification of the surviving fraction after concurrent treatment with DCB and TLZ (free) or nDCB and nTLZ (nanococktail).

A long-term growth assay was conducted at the 1:10 ratio in order to determine the optimal dosing strategy for the combination. It was found that sequential treatment with DCB or nDCB followed by TLZ or nTLZ treatment yielded insignificant growth inhibition compared to DMSO or nanoparticle vehicles, respectively (FIG. 6C and FIG. 6D). Treatment with TLZ and DCB concurrently resulted in 26±3% viability compared to DMSO controls while treatment with nTLZ and nDCB concurrently resulted in 16±5% viability compared to nanoparticle vehicle controls (FIG. 6C and FIG. 6D). In accordance with the dose response assays the combination of nTLZ+nDCB resulted in significantly lower viability compared to the combination of the free drugs (*p<0.05).

Figure 6E:
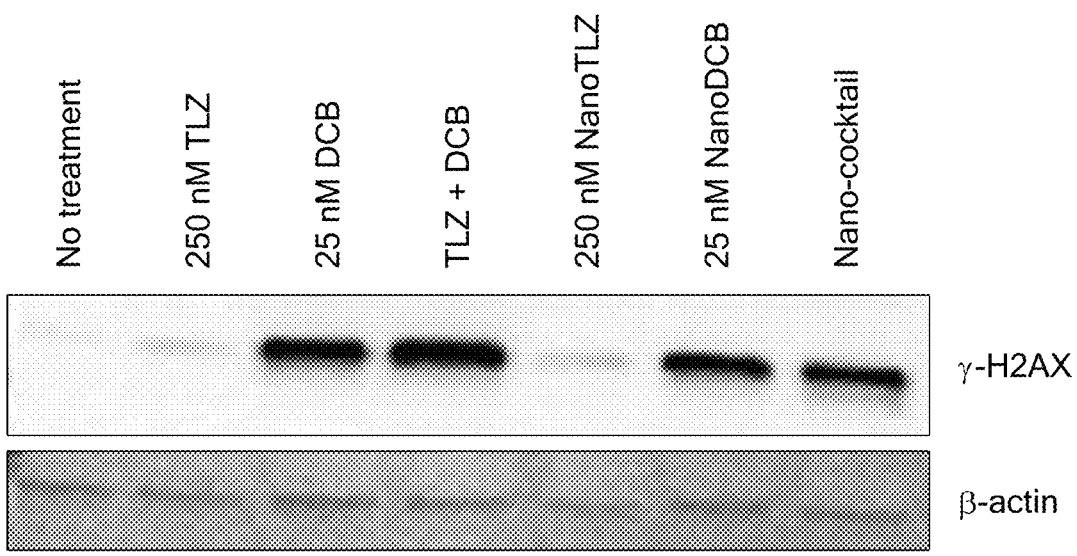
FIG. 6E shows representative western blots after a 48 hour exposure to the various treatments.

Biomarkers of DNA damage and apoptosis were assessed after a 48 hour drug treatment. DNA double strand breaks, monitored via γ-H2AX expression, were observed in all treatments. Treatments that included DCB or nDCB presented with much higher γ-H2AX expression compared to those treated with TLZ or nTLZ only (FIG. 6E). In accordance with the signs of DNA damage, apoptotic signaling, measured by cleaved PARP expression, is highest in conditions treated with DCB or nDCB.

The nanoformulation of DCB was synthesized in an effort to enhance efficacy while reducing toxicity such that the nanoformulation could be utilized with a previously developed nanoformulation of TLZ. In vitro assessment of the combination demonstrated TLZ+DCB and nTLZ+nDCB were synergistic at 3 different ratios, suggesting a viable combination. The long-term growth assay was conducted in order to determine the optimal dosing strategy for the combination. Parry et al. demonstrated the effect of DCB can persist for hours after treatment and that continuous exposure may not be necessary for activity [37]. Therefore, it was assessed whether it would be appropriate to pretreat with DCB to disrupt HR prior to treatment with TLZ. The sequential treatment with DCB or nDCB followed by TLZ and nTLZ was not found to be advantageous in regard to cell growth in vitro. In contrast, the simultaneous treatment with both compounds was extremely effective. Protein expression after drug exposure for 48 hours indicated both DNA damage and apoptotic signaling was depended on DCB or nDCB exposure. This is likely because TLZ induced genomic instability relies on an accumulation of DNA damage through a number of replication cycles and therefore more time is necessary to capture TLZ induced DNA damage.

Example 3: Pharmacokinetics and Pharmacodynamics

All animal studies were performed in accordance with protocols approved by the Institutional Animal Care and Use Committee (IACUC) at Northeastern University. Pharmacokinetic and pharmacodynamics studies were conducted for each individual formulation using orthotopic xenograft models of human TNBC. An orthotopic xenograft model of human TNBC was established via injection of 1×10$^6$ MDA-MB-231-LUC-D3H2LN (231) cells (cells were cultured in DMEM with 10% FBS and 1% Pen/Strep) in the mammary fat pad of female NCr-nu/nu mice (Charles River Laboratory).

Mice with tumors ~100 mm$^3$ in size were administered a single dose of 1 mg/kg i.v. NanoDCB or NanoTLZ. Mice were euthanized at designated time points (0.083, 0.5, 1, 6, and 24 hours for NanoDCB and 0.5, 1, 2, 4, 8, 24, 48, and 72 hours for NanoTLZ) after treatment for sample collection. Blood was collected via cardiac puncture into K2 EDTA microtainers. Blood was centrifuged at 1,600 g for 15 minutes at 4° C. Plasma was separated and frozen at −80° C. until processed. Acetonitrile was added to precipitate plasma proteins. Samples were centrifuged at 14,000 g for 5 minutes, and the supernatant was filtered with a 0.2 μm syringe filter. Each sample was dried overnight and reconstituted in 200 μL of acetonitrile for analysis via HPLC. HPLC conditions were as detailed in Example 5. A standard curve was prepared by processing plasma from untreated animals and spiking the samples with known amounts of DCB or TLZ when reconstituting the samples. FIG. 7A presents the TLZ levels (ng/mL) found in plasma after a single dose, resulting in a terminal half-life of 37.5 hours. FIG. 7B presents the DCB levels (μg/mL) in the plasma after a single dose, resulting in a half-life of 30.7 hours. PKSolver was used to fit the either a non-compartment model for NanoDCB or a two-compartment model for NanoTLZ [10].

Figure 8A:
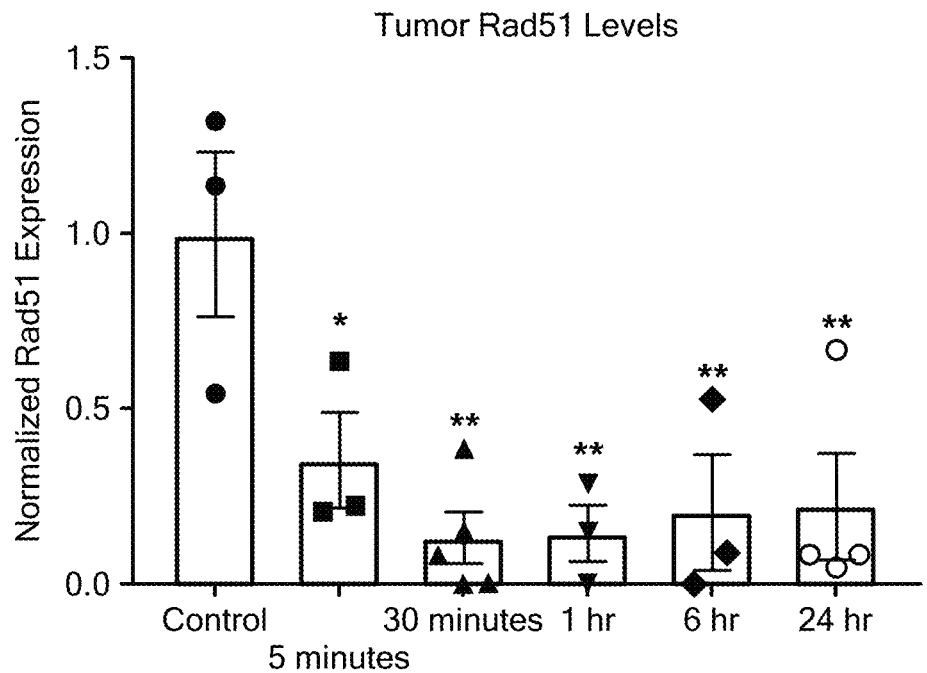
FIG. 8A and FIG. 8B plot the pharmacodynamics of the formulations in the nanococktail.

For example, pharmacokinetics and pharmacodynamics of nDCB were assessed after a single 1 mg/kg dose was administered (i.v.) to mice bearing 231 xenografts. Plasma was collected and DCB was extracted for HPLC analysis. The plasma data was assessed using non-compartmental analysis, the linear trapezoidal rule, and the half-life was determined to be 30.7 hours for nDCB (FIG. 7B). Tumors were extracted at the same time and flash frozen to stabilize protein levels. Western blotting was used to probe tumors for RAD51 levels to assess the timing in which nDCB is acting on the tumor and confirm disruption of HR, as hypothesized. Within 5 minutes of administration, RAD51 levels drop to less than 50% of the untreated tumors and continue to decrease to 13% 30 minutes after administration (FIG. 8A). RAD51 levels remain significantly lower than untreated controls for up to 24 hours after a single dose of nDCB (**$p<0.01$). Some tumors, 1 per group, did recover faster than others.

The tumors were collected and snap frozen in liquid nitrogen to stabilize protein expression (n=3-5/group) (26). Tumors were minced in lysis buffer (1% w/w deoxycholic acid, 1% w/w triton-x, 0.1% w/w sodium lauryl sulfate) with protease inhibitors (1 mM PMSF, 1 mM AEBSF.HCL, 800 nM aprotinin, 50 μM bestatin, 15 μM E-64, 5 mM EDTA, 20 μM leupeptin, and 10 μM pepstatin A). Total protein content was determined using the BCA assay. For tumors from animals treated with NanoDCB, levels of Rad51 in the tumor lysates were determined by western blotting. 40 μg of protein was separated on 4-20% polyacrylamide gels and transferred to PDVF membranes. Rad51 (Santa Cruz, 1:200) and β-actin (Santa Cruz, 1:1000) primary antibodies were used to detect the corresponding proteins. The secondary antibody was HRP-linked anti-mouse (Santa Cruz, 1:2000) and ECL substrate was used for detection. Images representative of samples from each group were analyzed. ImageJ software was used to quantify protein expression. RAD51 levels were internally normalized to β-ACTIN and normalized levels were compared to the average control expression.

For tumors collected from animals treated with NanoTLZ levels of PAR in the tumor, lysates were determined by ELISA using PARP in vivo PD Assay II kit (Trevigen) following the manufacturer's instructions. PAR levels in lysates were confirmed using western blot.

Figure 8B:
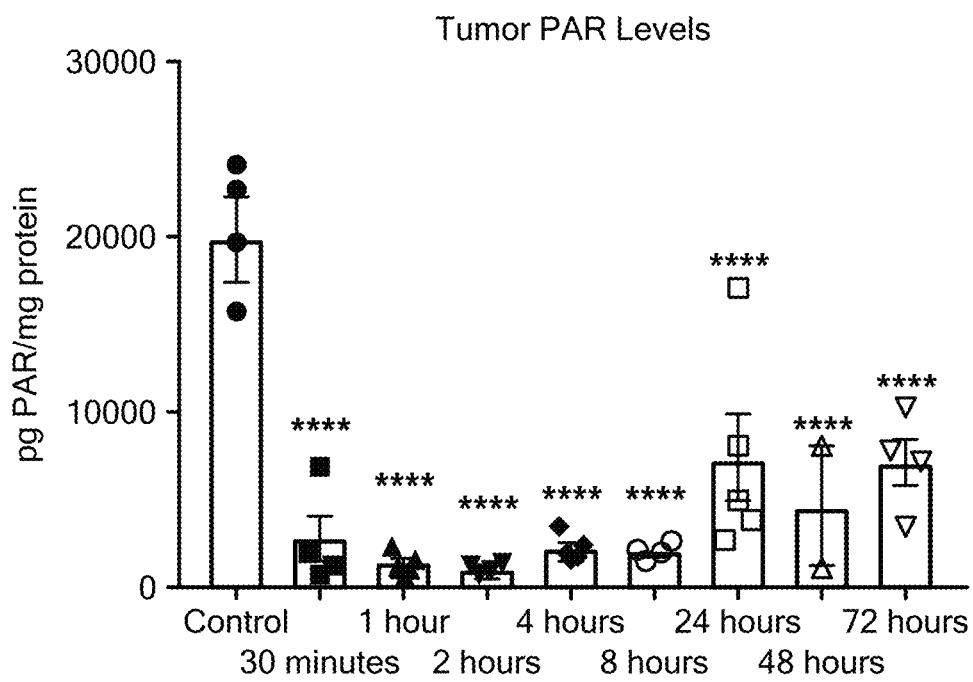

FIG. 7B shows (pharmacokinetics) demonstrating nDCB is long-circulating. Pharmacodynamics is assessed by RAD51 levels in tumors revealing DCB is disrupting HR in the tumors; *, $p<0.05$; **, $p<0.01$ vs control. FIG. 8A demonstrates nanoDCB starts to downregulate Rad51 in the tumor within 5 minutes of administration, and stably disrupts Rad51 for up to 24 hours. FIG. 8B shows the tumor PAR levels and demonstrates nanoTLZ begins acting in the tumor within 30 minutes of administration and stably depleted PAR levels for at least 8 hours.

Example 4: Therapeutic Efficacy of Nanococktail

The therapeutic efficacy of the combination of the nanococktail was assessed in orthotopic MDA-MB-231-D3H2LN-LUC xenografts. $1\times10^6$ cells in 50% matrigel (Corning) were implanted in the mammary fat pad of female NCr-nu/nu mice. When tumors reached between 50-100 mm³, mice were randomized into 8 groups: no treatment (n=6), vehicle (n=6), free TLZ (n=6), free DCB (n=6), free TLZ+free DCB (n=10), NanoTLZ (n=6), NanoDCB (n=6), and and nTLZ+nDCB in nanococktail (n=10). Treatments were administered i.v. at a dose of 0.33 mg/kg for TLZ formulations and 1.0 mg/kg for DCB formulations. Vehicle treatments were the volume equivalent of each empty nanoparticle, to match the treatment of the combination nanotherapy group. All treatments were prepared immediately prior to each administration. Animals were treated every other day until tumors reached 1000 mm³. Animals were weighed and tumors measured using calipers during each treatment. In FIG. 9A, tumor volume was calculated using the following formula: $V=0.5\times L\times W^2$, where L was the longest dimension and W was the dimension perpendicular to L.

Figure 9B:
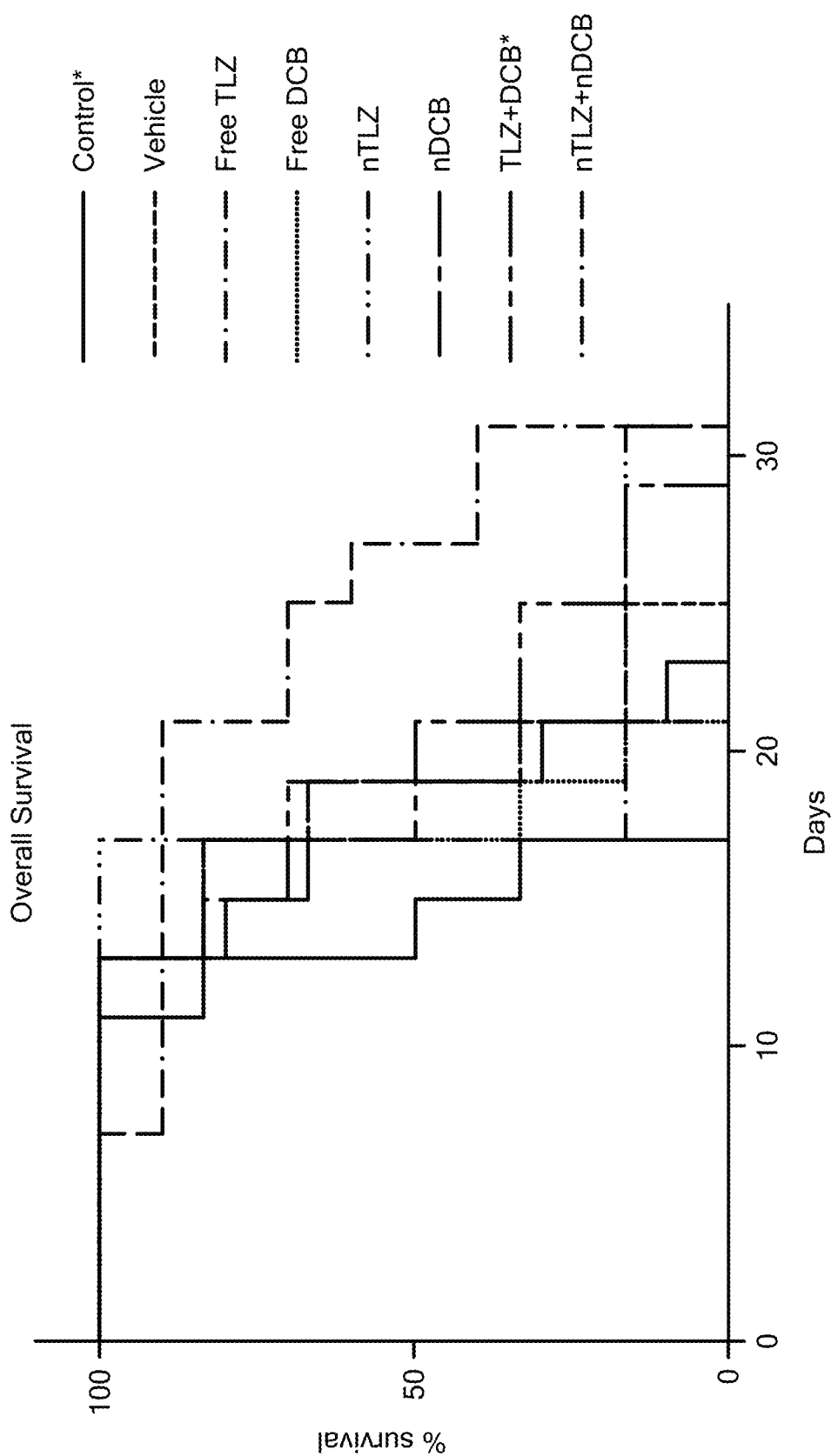
FIG. 9B shows overall survival over time during treatment with a nanococktail, the free drugs at the same dose, or the single agents.

The mice bearing 231 xenografts were treated with either 0.33 mg/kg TLZ or nTLZ (i.v.) or 1.0 mg/kg DCB or nDCB (i.v.) every other day. The combination treatments, free TLZ and DCB, or nTLZ+nDCB, were administered on the same schedule with the same dosing. The vehicle group consisted of a volume equivalent to the nTLZ carrier and the nDCB carrier system. Untreated tumors grew exponentially, resulting in a mean survival of 14.3±2.4 days for the control animals. While the various treatments slowed tumor growth compared to the controls, nTLZ+nDCB was the only treatment to have a significant effect (FIG. 9A, FIG. 9B). After 3 weeks of treatment, day 19, the tumor volume was significantly lower for mice treated with nTLZ+nDCB, compared to both control groups (**, $p<0.01$), both free drug monotherapies (*, $p<0.05$ vs. DCB and *, $p<0.001$ vs. TLZ), and the free drug combination therapy (, $p<0.01$) (FIG. 9A). The relative tumor volume as assessed by fold change was significantly lower for the nanoformulation combination, 5.3±0.6, compared to the combination of free TLZ and free DCB, 8.9±0.4 (*$p<0.05$). Although nTLZ+nDCB did not induce regression, it did extend survival time compared to the free combination, with a median survival time of 26 days vs. 19 days (FIG. 9B, *$p<0.05$).

Body weight was measured daily and on average no significant weight loss was observed. One animal in the nTLZ+nDCB group did experience a 20% loss in body weight 7 days after treatment initiation, and was euthanized (FIG. 9B). To assess potential hematologic toxicities after treatment animals were treated with 3 doses of either TLZ and DCB or nTLZ+nDCB. 24 hours after the final dose blood was collected and complete blood count assessed white blood cell (WBC), red blood cell (RBC) and platelet (PLT) counts. Neither of the combination drug treatments resulted in a significant difference in WBC, RBC, or PLT counts compared to vehicle (FIGS. 10A-10C).

To study toxicity, mice bearing 231 tumors were treated with either 3 doses of empty nanoparticles (n=3), free TLZ and free DCB (n=4), or nTLZ and nDCB (n=4). 24 hours after the final treatment animals were euthanized and blood collected via cardiac puncture into K2 EDTA microtainers. All samples were immediately sent to VRL labs for complete blood count.

The nanococktail was well tolerated, suggesting possible dose-amplification in this co-administered formulation. These data highlight the ability to utilize nanococktails at lower doses than with the free drugs, potentially bypassing the need for dose reduction or delay in the clinic.

At the endpoint livers, kidneys, and spleens were collected from animals in all groups to assess nanoparticle related toxicity. H&E staining revealed no significant morphological changes in these tissues (FIG. 10D). To examine histology, liver, kidneys, and spleen were harvested during necropsy and fixed in 10% formalin. Harvested tissues were embedded in paraffin, cut, and stained by the Dana-Farber/Harvard Cancer Center Research Pathology Core. Slices of the organs were stained with hematoxylin and eosin (H&E).

The nDCB, a polymeric formulation of DCB, which when administered as part of a nanococktail with nTLZ elicited a therapeutic effect in TNBC xenografts. nDCB extends the half-life of DCB considerably compared to the reported half-life of free DCB. Pharmacodynamics (PD) reveal nDCB and nTLZ both inhibit their targets in the tumor for up to 24 hours after administration. An orthotopic model of TNBC was generated in mice to test the effect of nTLZ+nDCB compared to the free drug cocktail in tumors with no known defects in HR. Complete blood count was assessed for nTLZ+nDCB and free TLZ+free DCB to determine whether these doses elicited any hematologic toxicity. The results of these experiments demonstrate the nanococktail can be a promising strategy for combining two drugs with different pharmacokinetics (PK) in order to produce a similar PK/PD relationship and offer therapeutic benefit at lower doses.

Example 5: Physicochemical Characterization of Formulations

Figure 3B:
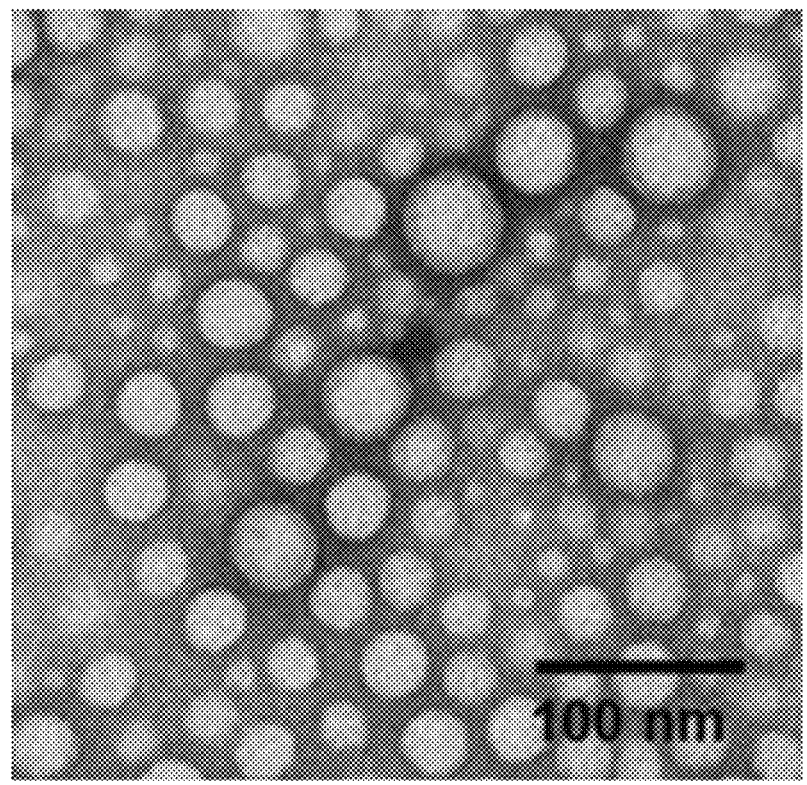
FIG. 3B presents a transmission electron micrograph of nDCB polymeric nanoparticles. The scale bar is 100 nm.
Figure 3C:
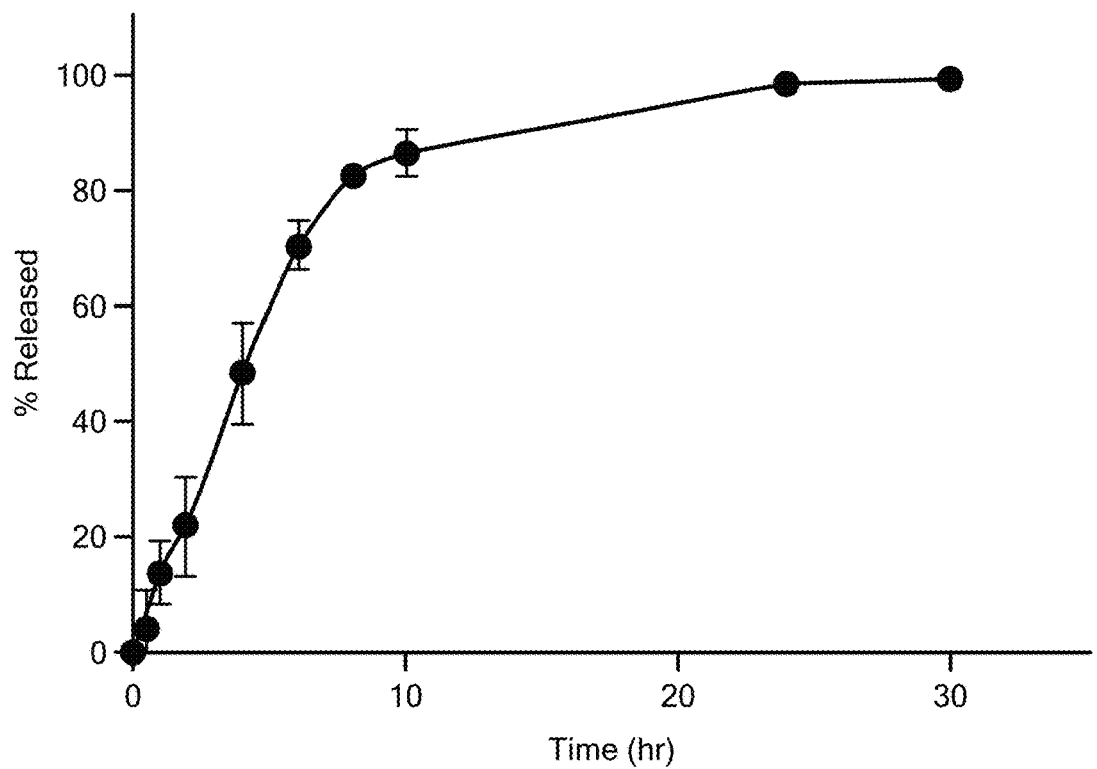
FIG. 3C is a plot of release kinetics of nDCB at 37° C. under constant agitation.
Figure 3D:
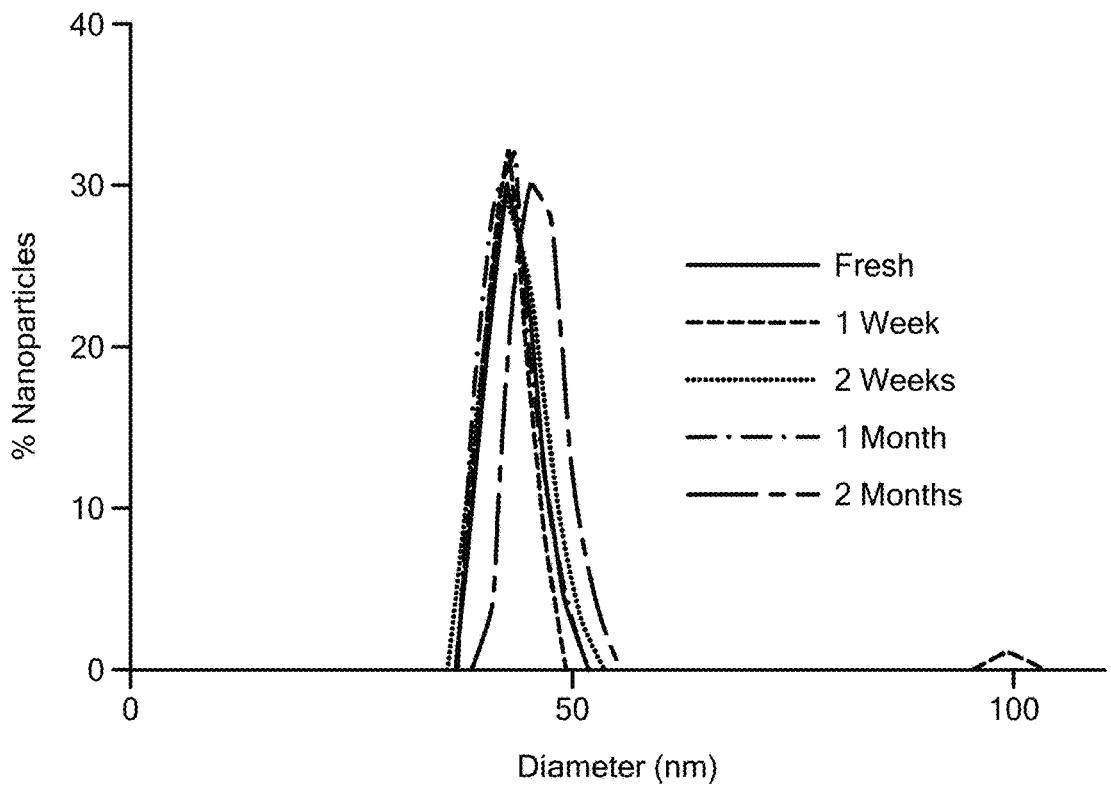
FIG. 3D is a plot of particle size measured by DLS of nDCB at time zero, 1 week, 2 weeks, 1 month, and 2 months stored at 4° C.
Figure 3E:
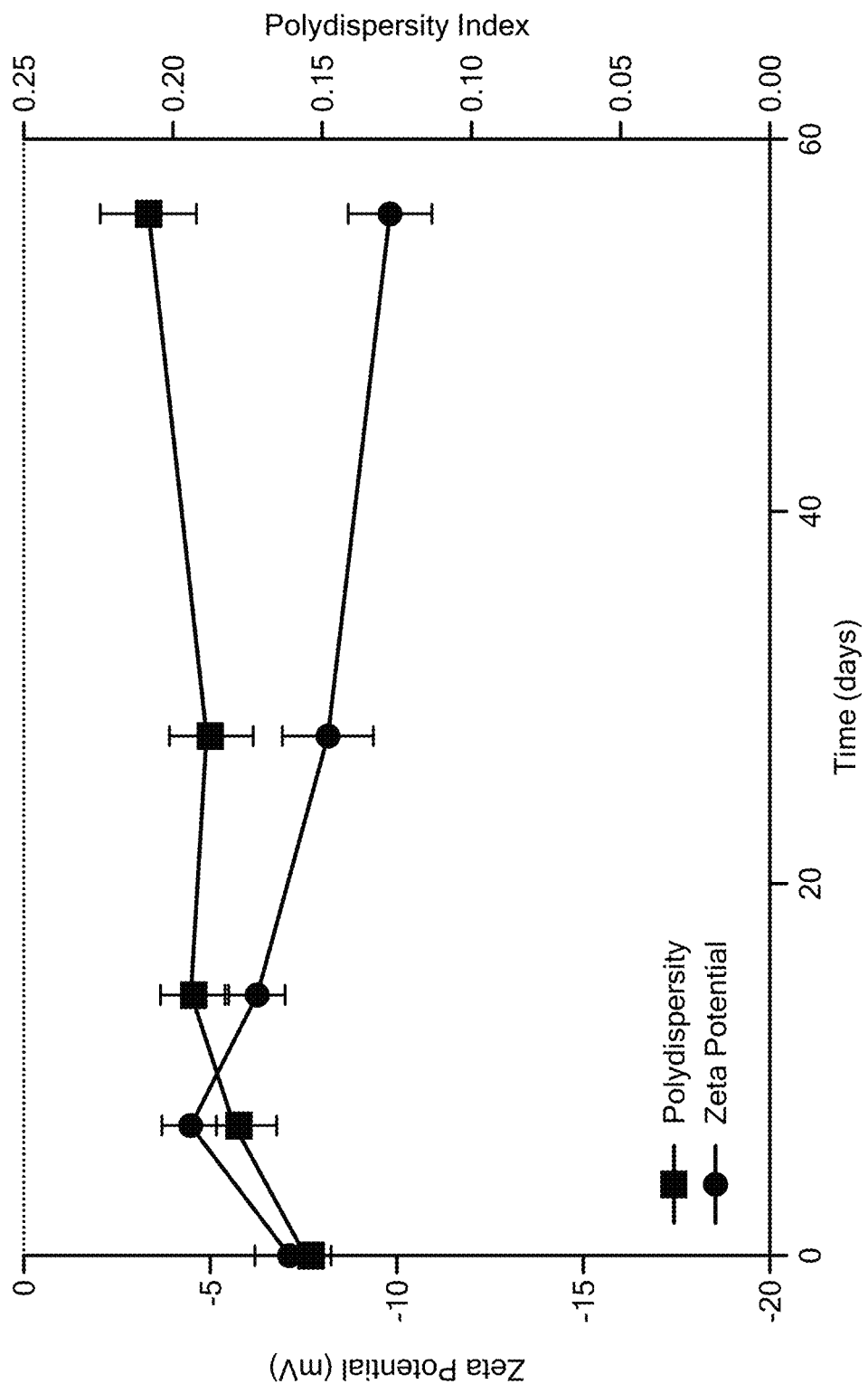
FIG. 3E is a plot of zeta potential (dark line) and polydispersity index (gray line) for nDCB stored at 4° C.
Figure 4B:
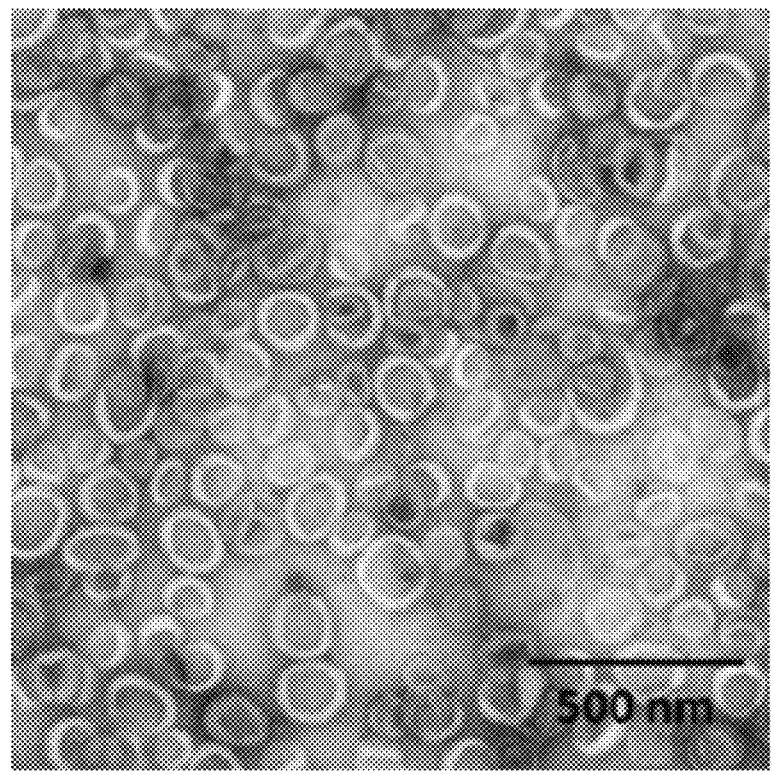
FIG. 4B presents a transmission electron micrograph of liposomal nanoparticles from Example 1. The scale bar is 500 nm.
Figure 5A:
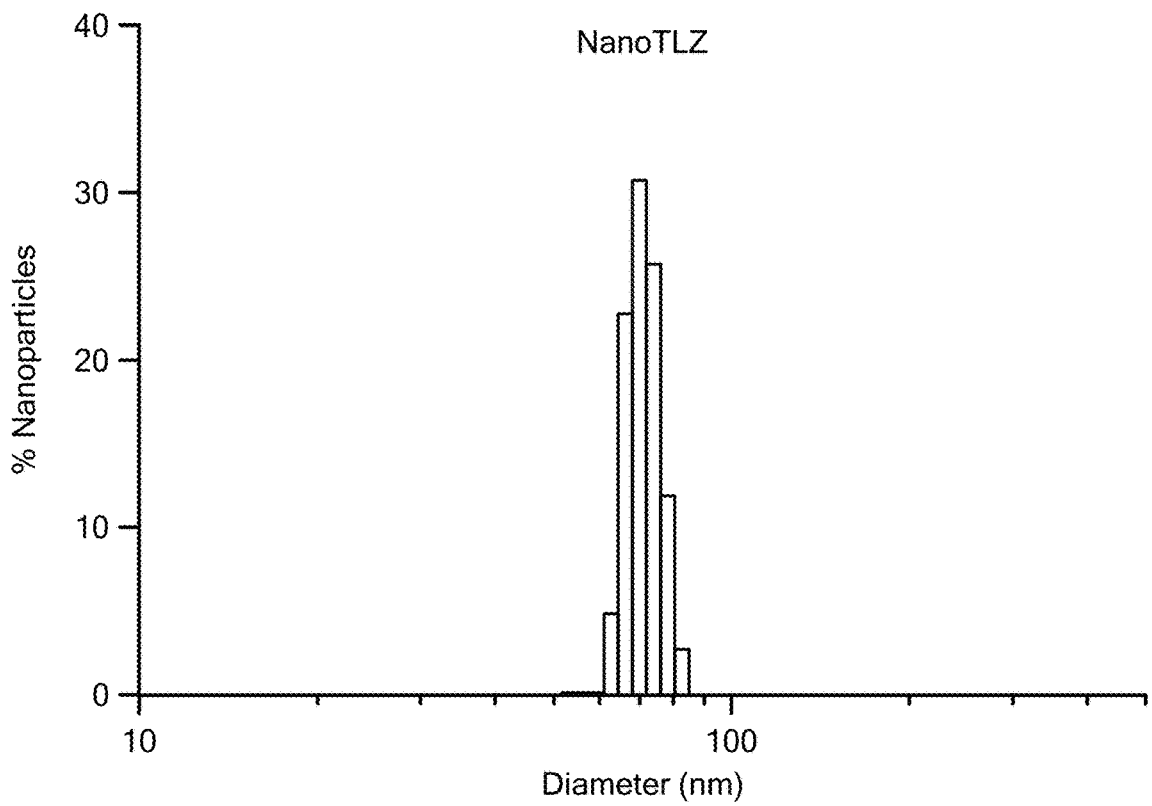
FIG. 5A demonstrates the size distribution of nanoTLZ.
Figure 5B:
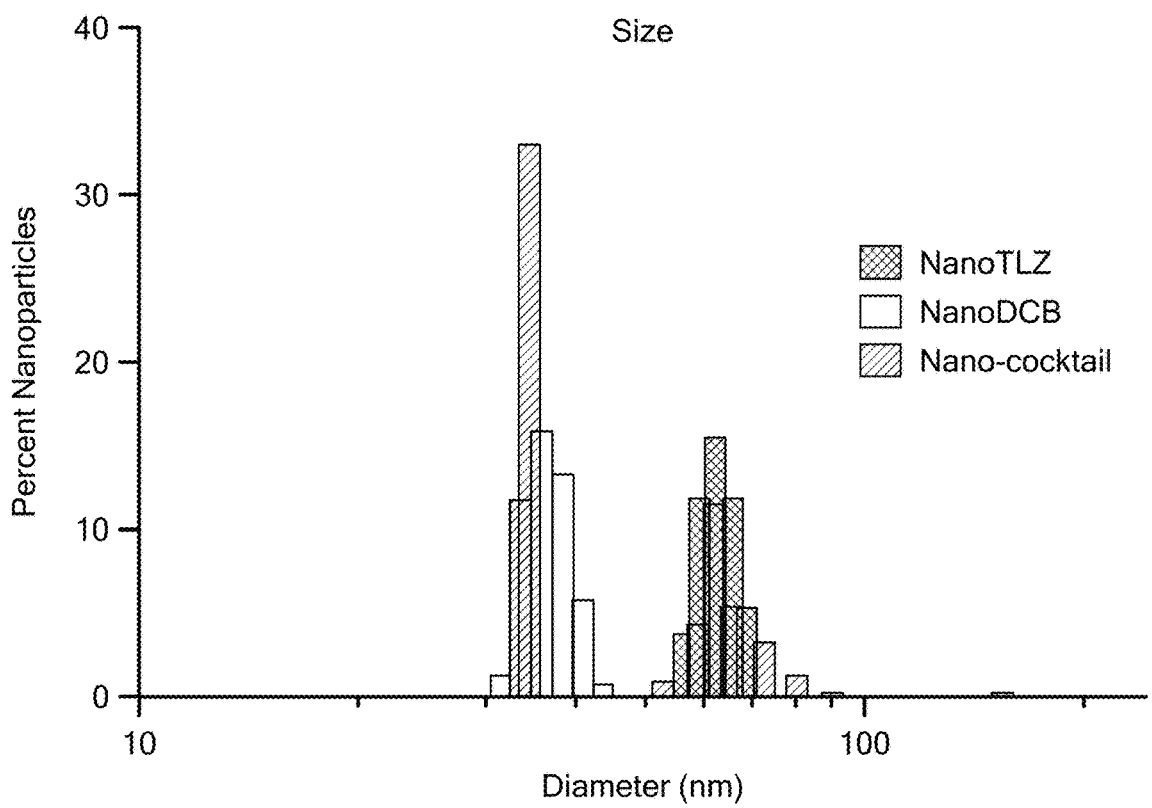
FIG. 5B demonstrates an overlay of the size distributions of nanoTLZ, nanoDCB and a nanococktail.

Size and zeta potential of the nanoparticles were measured using a Brookhaven 90Plus analyzer (dynamic light scattering) equipped with ZetaPALS. Nanoparticles were diluted 1:100 in PBS for all measurements. Size was confirmed by Transmission Electron Microscopy (TEM) with a negative stain of 1.5% uranyl acetate (FIG. 3B, FIG. 4B).

The concentration of encapsulated dinaciclib was measured by lysing nanoparticles with acetonitrile prior to High Performance Liquid Chromatography (HPLC) analysis. HPLC was performed on an Agilent 1260 Infinity II with a ZORBAX 300 StableBond C18 column. The mobile phase A consisted of acetonitrile with 0.1% trifluoroacetic acid, and the mobile phase B consisted of water with 0.1% trifluoroacetic acid. An isocratic elution was carried out at a ratio of 80:20 A:B. The flow rate was 1.8 mL/minute and dinaciclib was detected with a wavelength of 254 nm at ~0.84 minutes.

The concentration of encapsulated talazoparib was measured by lysing nanoparticles with methanol prior to HPLC analysis with a reverse phase C18 Supelco column. The mobile phase A consisted of acetonitrile with 0.1% phosphoric acid, and the mobile phase B consisted of water with 0.1% phosphoric acid. The following gradient was applied 10-95% A (0-5.3 min), 95% A (5.3-8.5 min), 95-10% A (8.5-10.0 min), 10% A (10-11.5 min). The flow rate was 0.82 mL/minute and talazoparib was detected with a wavelength of 309 nm at ~4.2 minutes.

Statistical Analysis

All in vitro data were plotted as mean±SD. The statistical significance of in vitro data was determined by using Student's t-tests with $\alpha=0.05$ for significance. All in vivo data were plotted as mean±SEM. Normality of all data was tested with the D'Agostino-Pearson test and p<0.05 not considered a normal distribution. All data followed a normal distribution and significance was tested with one-way ANOVA followed by Tukey's test for significance with $\alpha=0.05$. The log-rank test with the Bonferroni correction for multiple comparisons was used to assess family-wise significance of survival curves.

REFERENCES

1. Hong S I, Ryu B H, Chong Y P, et al. Five severe COVID-19 pneumonia patients treated with triple combination therapy with lopinavir/ritonavir, hydroxychloroquine, and interferon β-1b. *Int J Antimicrob Agents*. 2020; 56(2):106052. doi:10.1016/j.ijantimicag.2020.106052.
2. Bassetti, M. & Righi, E. New antibiotics and antimicrobial combination therapy for the treatment of gram-negative bacterial infections. *Curr. Opin. Crit. Care* 21, 402-411 (2015).
3. Lyle, T. A. Ribonucleic Acid Viruses: Antivirals for Human Immunodeficiency Virus. *Compr. Med. Chem. II* 329-371 (2007). doi:10.1016/B0-08-045044-X/00213-3
4. Margulies, S. et al. Combination Therapies for Traumatic Brain Injury: Retrospective Considerations. *J. Neurotrauma* 33, 101-112 (2016).
5. Lewis, D. R. et al. Nanotherapeutics for inhibition of atherogenesis and modulation of inflammation in atherosclerotic plaques. *Cardiovasc. Res.* 109, 283-293 (2016).
6. Dhawan, M. et al. Efficacy and hematologic toxicity of carboplatin and talazoparib combination therapy in BRCA mutated patients. in *J Clin Oncol* 34, 2016 (suppl; abstr 2557) (2016).
7. Rajan, A. et al. A phase I combination study of olaparib with cisplatin and gemcitabine in adults with solid tumors. *Clin. Cancer Res.* 18, 2344-2351 (2012).
8. De Jong, W. H. & Borm, P. J. a. Drug delivery and nanoparticles:applications and hazards. *Int. J. Nanomedicine* 3, 133-149 (2008).
9. Davis, M. E., Chen, Z. & Shin, D. M. Nanoparticle therapeutics: an emerging treatment modality for cancer. *Nat. Rev. Drug Discov.* 7, 771-782 (2008).
10. Zhang, Y., Huo, M., Zhou, J. & Xie, S. PKSolver: An add-in program for pharmacokinetic and pharmacodynamic data analysis in Microsoft Excel. *Comput. Methods Programs Biomed.* 99, 306-314 (2010).
11. Bauer K R, Brown M, Cress R D, Parise C A, Caggiano V. Descriptive analysis of estrogen receptor (ER)-negative, progesterone receptor (PR)-negative, and HER2-negative invasive breast cancer, the so-called triple-negative phenotype: A population-based study from the California Cancer Registry. Cancer. 2007; 109:1721-8.
12. Szekely B, Silber A L M, Pusztai L. New Therapeutic Strategies for Triple-Negative Breast Cancer. Oncology (Williston Park) [Internet]. 2017 [cited 2018 Oct. 5]; 31:130-7. Available from: ncbi.nlm.nih.gov/pubmed/28205193
13. Lee A, Djamgoz M B A. Triple negative breast cancer: Emerging therapeutic modalities and novel combination therapies. Cancer Treat Rev. 2018; 62:110-22.
14. Hartman A-R, Kaldate R R, Sailer L M, Painter L, Grier C E, Endsley R R, et al. Prevalence of BRCA mutations in an unselected population of triple-negative breast cancer. Cancer [Internet]. 2012; 118:2787-95. Available from: doi.wiley.com/10.1002/cncr.26576
15. Gonzalez-Angulo A M, Timms K M, Liu S, Chen H, Litton J K, Potter J, et al. Incidence and Outcome of BRCA Mutations in Unselected Patients with Triple Receptor-Negative Breast Cancer. Clin Cancer Res [Internet]. 2011; 17:1082-9. Available from: clincancerres.aacrjournals.org/cgi/doi/10.1158/1078-0432.CCR-10-2560
16. Farmer H, McCabe N, Lord C J, Tutt A N J, Johnson D A, Richardson T B, et al. Targeting the DNA repair defect in BRCA mutant cells as a therapeutic strategy. Nature [Internet]. 2005 [cited 2014 Jul. 10]; 434:917-21. Available from: ncbi.nlm.nih.gov/pubmed/15829967
17. Bryant H E, Schultz N, Thomas H D, Parker K M, Flower D, Lopez E, et al. Specific killing of BRCA2-deficient tumours with inhibitors of poly(ADP-ribose) polymerase. Nature [Internet]. 2005 [cited 2015 Jan. 2]; 434:913-7. Available from: ncbi.nlm.nih.gov/pubmed/15829966
18. Johnson N, Cai D, Kennedy R D, Pathania S, Arora M, Li Y C, et al. Cdk1 Participates in BRCA1-Dependent S Phase Checkpoint Control in Response to DNA Damage. Mol Cell [Internet]. Elsevier Ltd; 2009; 35:327-39. Available from: dx.doi.org/10.1016/j.molcel.2009.06.036

19. Johnson N, Li Y C, Walton Z E, Cheng K A, Li D, Rodig S J, et al. Compromised CDK1 activity sensitizes BRCA-proficient cancers to PARP inhibition. Nat Med [Internet]. Nature Publishing Group; 2011; 17:875-82. Available from: dx.doi.org/10.1038/nm.2377
20. Johnson S F, Cruz C, Greifenberg A K, Dust S, Stover D G, Chi D, et al. CDK12 Inhibition Reverses De Novo and Acquired PARP Inhibitor Resistance in BRCA Wild-Type and Mutated Models of Triple-Negative Breast Cancer. Cell Rep. 2016; 17:2367-81.
21. Alagpulinsa D, Ayyadevara S, Yaccoby S, shmookler Reis R. Dinaciclib, a CDK Inhibitor, Impairs Homologous Recombination and Sensitizes Multiple Myeloma Cells to PARP Inhibition. Mol Cancer Ther [Internet]. 2016; 15:241-50. Available from: bloodjournal.org/content/124/21/479.abstract
22. Carey J P W, Karakas C, Bui T, Chen X, Vijayaraghavan S, Zhao Y, et al. Synthetic lethality of PARP inhibitors in combination with MYC blockade is independent of BRCA status in triple-negative breast cancer. Cancer Res. 2018; 78:742-57.
23. Horiuchi D, Kusdra L, Huskey N E, Chandriani S, Lenburg M E, Gonzalez-Angulo A M, et al. MYC pathway activation in triple-negative breast cancer is synthetic lethal with CDK inhibition. J Exp Med [Internet]. 2012; 209:679-96. Available from: jem.org/lookup/doi/10.1084/jem.20111512
24. Jou Y-M, Kirschmeier P, Yao S-L, Statkevich P, Zhang D, Small K A, et al. A first-inhuman, phase 1, dose-escalation study of dinaciclib, a novel cyclin-dependent kinase inhibitor, administered weekly in subjects with advanced malignancies. J Transl Med. 2013; 11:259.
25. Mita M M, Joy A A, Mita A, Sankhala K, Jou Y-M, Zhang D, et al. Randomized Phase II Trial of the Cyclin-Dependent Kinase Inhibitor Dinaciclib (MK-7965) Versus Capecitabine in Patients With Advanced Breast Cancer. Clin Breast Cancer [Internet]. 2014 [cited 2019 Feb. 26]; 14:169-76. Available from: ncbi.nlm.nih.gov/pubmed/24393852
26. Mita M M, Mita A C, Moseley J L, Poon J, Small K A, Jou Y M, et al. Phase 1 safety, pharmacokinetic and pharmacodynamic study of the cyclin-dependent kinase inhibitor dinaciclib administered every three weeks in patients with advanced malignancies. Br J Cancer [Internet]. Nature Publishing Group; 2017; 117:1258-68. Available from: dx.doi.org/10.1038/bjc.2017.288
27. Shapiro G I, Do K T, Tolaney S M, Hilton J F, Cleary J M, Wolanski A, et al. Abstract CT047: Phase 1 dose-escalation study of the CDK inhibitor dinaciclib in combination with the PARP inhibitor veliparib in patients with advanced solid tumors. Cancer Res [Internet]. American Association for Cancer Research; 2017 [cited 2018 Oct. 5]; 77:CT047-CT047. Available from: cancerres.aacrjournals.org/lookup/doi/10.1158/1538-7445.AM2017-CT047
28. Murai J, Huang S Y N, Das B B, Renaud A, Zhang Y, Doroshow J H, et al. Trapping of PARP1 and PARP2 by clinical PARP inhibitors. Cancer Res. 2012; 72:5588-99.
29. Lord C J, Ashworth A. PARP inhibitors: Synthetic lethality in the clinic. Science (80-) [Internet]. 2017; 355:1152-8. Available from: sciencemag.org/lookup/doi/10.1126/science.aam7344
30. Matulonis U. Novel combination strategies for recurrent ovarian cancer. 12th Bienn Ovarian Cancer Res Symp. Seattle; 2018.
31. Zhang D, Baldwin P, Leal A S, Carapellucci S, Sridhar S, Liby K T. A nano-liposome formulation of the PARP inhibitor Talazoparib enhances treatment efficacy and modulates immune cell populations in mammary tumors of BRCA-deficient mice. Theranostics. 2019; Accepted.
32. Rapid Manufacture of Hydrophobic Drug-Loaded Liposomes. Precision Nanosystems; 2016.
33. Baldwin P, Ohman A, Medina J, McCarthy E, Dinulescu D, Sridhar S. Nanoformulation of Talazoparib Delays Tumor Progression and Ascites Formation in a Late Stage Cancer Model. Front Oncol. 2019; 9.
34. Chou T-C, Martin N. CompuSyn for Drug Combinations and for General Dose-Effect Analysis. 2005; 1-68. Available from: combosyn.com
35. Kinders R J, Hollingshead M, Khin S, Rubinstein L, Tomaszewski J E, Doroshow J H, et al. Preclinical Modeling of a Phase 0 Clinical Trial: Qualification of a Pharmacodynamic Assay of Poly (ADP-Ribose) Polymerase in Tumor Biopsies of Mouse Xenografts. Clin Cancer Res [Internet]. 2008; 14:6877-85. Available from: clincancerres.aacrjournals.org/cgi/doi/10.1158/1078-0432.CCR-08-0214
36. Davarinejad H. Quantifications of Western Blots with ImageJ [Internet]. Available from: rsb.info.nih.gov/ij/
37. Parry D, Guzi T, Shanahan F, Davis N, Prabhavalkar D, Wiswell D, et al. Dinaciclib (SCH 727965), a Novel and Potent Cyclin-Dependent Kinase Inhibitor. Mol Cancer Ther [Internet]. 2010; 9:2344-53. Available from: mct.aacrjournals.org/cgi/doi/10.1158/1535-7163.MCT-10-0324
38. Castroviejo-Bermejo M, Cruz C, Llop-Guevara A, Gutiérrez-Enríquez S, Ducy M, Ibrahim Y H, et al. A RAD51 assay feasible in routine tumor samples calls PARP inhibitor response beyond BRCA mutation. EMBO Mol Med [Internet]. John Wiley & Sons, Ltd; 2018 [cited 2019 Aug. 7]; 10:e9172. Available from: embomolmed.embopress.org/lookup/doi/10.15252/emmm.201809172
39. Litton J K, Rugo H S, Ettl J, Hurvitz S A, Gonçalves A, Lee K-H, et al. Talazoparib in Patients with Advanced Breast Cancer and a Germline BRCA Mutation. N Engl J Med [Internet]. 2018; NEJMoa1802905. Available from: nejm.org/doi/10.1056/NEJMoa1802905

The invention claimed is:

1. A pharmaceutical formulation comprising: a synergistically anti-tumor effective amount of a first nanoparticulate delivery vehicle and a second nanoparticulate delivery vehicle;
   a first nanoparticulate delivery vehicle comprising a first active agent; and
   a second nanoparticulate delivery vehicle comprising a second active agent;
   wherein the first active agent is dinaciclib and the first nanoparticulate delivery vehicle further comprise poly (D,L-lactide-co-glycolide (PLGA) and methoxy poly (ethylene glycol)-b-poly(lactic-co-glycolic acid) (mPEG-PLGA);
   wherein the second active agent is talazoparib and the second nanoparticulate delivery vehicle comprises 1,2-dipalmitoyl-sn-glycero-3-phophatidylcholine (DPPC), 1,2-dioleoyl-3-tri methylammonium propane (DO-TAP), cholesterol, and 1,2-distearoyl-sn-glycero-3 phosphatidylethanolamine-N-(methoxy(polyethyleneglycol) (DSPE-PEG); and
   wherein the first and second delivery vehicles each have a zeta potential, and the zeta potentials of the first and second nanoparticulate delivery vehicles differ by not more than about 40 mV.

2. The pharmaceutical formulation of claim 1, wherein the zeta potential of the first nanoparticulate delivery vehicle and the zeta potential of the second nanoparticulate delivery vehicle differ by not more than about 15 mV.

3. The pharmaceutical formulation of claim 1 which is a liquid suspension of said nanoparticulate delivery vehicles.

4. The pharmaceutical formulation of claim 1 which is a solid composition comprising said nanoparticulate delivery vehicles embedded in a biodegradable polymer matrix.

5. The pharmaceutical formulation of claim 1, wherein the first nanoparticulate delivery vehicle and the second nanoparticulate delivery vehicle each have an average diameter in the range from about 10 nm to about 900 nm.

6. The pharmaceutical formulation of claim 5, wherein the average diameters of the first and second nanoparticulate delivery vehicles do not increase more than 10% upon storage for 24 hours at a temperature in the range from about 4° C. to about 20° C. after they are mixed to produce the formulation.

7. The pharmaceutical formulation of claim 1, wherein the proportion of the first nanoparticulate delivery vehicle to the second nanoparticulate delivery vehicle is in the range from about 1 to about 1:10 on a weight or molar basis for the first and second active agents.

8. A method of treating cancer, the method comprising administering the pharmaceutical formulation of claim 1 to a subject in need thereof.

9. A pharmaceutical kit comprising:
 a first nanoparticulate delivery vehicle comprising a first active agent; and
 a second nanoparticulate delivery vehicle comprising a second active agent;
 wherein the first active agent is dinaciclib and the first nanoparticulate delivery vehicle further comprises poly (D,L-lactide-co-glycolide (PLGA) and methoxy poly (ethylene glycol)-b-poly(lactic-co-glycolic acid) (mPEG-PLGA);
 wherein the second active agent is talazoparib and the second nanoparticulate delivery vehicle comprises 1,2-dipalmitoyl-sn-glycero-3-phophatidylcholine (DPPC), 1,2-dioleoyl-3-tri methylammonium propane (DOTAP), cholesterol, and 1,2-distearoyl-sn-glycero-3 phosphatidylethanolamine-N-(methoxy(polyethyleneglycol) (DSPE-PEG); and
 wherein the first and second delivery vehicles each have a zeta potential, and the zeta potentials of the first and second nanoparticulate delivery vehicles differ by not more than about 40 mV;
 wherein the first and second delivery vehicles are configured for coordinated delivery of the first and second active agents in an anti-tumor effective amount when the first and second delivery vehicles are administered to a subject in need thereof; and
 wherein the first and second nanoparticulate delivery vehicles are provided in separate containers.

* * * * *